United States Patent
Carling et al.

(10) Patent No.: US 6,828,322 B2
(45) Date of Patent: Dec. 7, 2004

(54) TRIAZOLO-PYRIDAZINE DERIVATIVES AS LIGANDS FOR GABA RECEPTORS

(75) Inventors: William Robert Carling, Bishops Stortford (GB); Jose Luis Castro Pineiro, Bishops Stortford (GB); Ian James Collins, Ware (GB); Alexander Richard Guiblin, Welwyn Garden City (GB); Timothy Harrison, Great Dunmow (GB); Andrew Madin, Sawbridgeworth (GB); Kevin William Moore, Buntingford (GB); Michael Geoffrey Russell, Welwyn Garden City (GB); Gayle Scott, Lanark (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/463,075

(22) Filed: Jun. 17, 2003

(65) Prior Publication Data

US 2004/0063714 A1 Apr. 1, 2004

Related U.S. Application Data

(62) Division of application No. 09/582,589, filed as application No. PCT/GB99/00103 on Jan. 13, 1999, now Pat. No. 6,579,875.

(30) Foreign Application Priority Data

Jan. 21, 1998 (GB) .............................................. 9801233
Oct. 2, 1998 (GB) .............................................. 9821517

(51) Int. Cl.[7] .................... A61K 31/5025; C07D 487/04
(52) U.S. Cl. ....................................... 514/248; 544/236
(58) Field of Search ........................... 514/248; 544/236

(56) References Cited

U.S. PATENT DOCUMENTS

| | | | |
|---|---|---|---|
| 4,112,095 A | 9/1978 | Allen, Jr. et al. | |
| 4,117,130 A | 9/1978 | Allen, Jr. et al. | |
| 4,230,705 A | 10/1980 | Allen, Jr. et al. | |
| 4,260,755 A | 4/1981 | Moran et al. | |
| 4,260,756 A | 4/1981 | Moran et al. | |
| 4,654,343 A | 3/1987 | Albright et al. | |
| 6,255,305 B1 | 7/2001 | Broughton et al. | |
| 6,579,875 B1 | 6/2003 | Carling et al. | |

FOREIGN PATENT DOCUMENTS

| | | |
|---|---|---|
| DE | 27 41 763 | 9/1977 |
| EP | 0 085 840 | 8/1983 |
| EP | 0 134 946 | 3/1985 |
| GB | 1 589 237 | 5/1991 |
| WO | WO 98/04559 | 2/1998 |

OTHER PUBLICATIONS

Bayley, et al., J. Psychopharmacol., 10: 206–213 (1996).
Bristow, et al., J. Pharmacol. Exp. Ther., 279: 492–501 (1996).
Dawson, et al., Psychoparmacology, 121: 109–117 (1995).

*Primary Examiner*—Emily Bernhardt
(74) *Attorney, Agent, or Firm*—J. Eric Thies; Melvin Winokur

(57) ABSTRACT

A class of substituted 1,2,4-triazolo[4,3-b]pyridazine derivatives, possessing a fluoro-substituted phenyl ring at the 3-position and a heteroaryl-methoxy moiety at the 6-position, are selective ligands for $GABA_A$ receptors, in particular having high affinity for the α2 and/or α3 subunit thereof, and are accordingly of benefit in the treatment and/or prevention of disorders of the central nervous system, including anxiety and convulsions.

15 Claims, No Drawings

TRIAZOLO-PYRIDAZINE DERIVATIVES AS LIGANDS FOR GABA RECEPTORS

CROSS REFERENCE TO RELATED APPLICATIONS

This application is a division of application Ser. No. 09/582,589, filed Jun. 28, 2000, now U.S. Pat. No. 6,579,875, which is an application under 35 U.S.C. § 371 of PCT Application No. PCT/GB99/00103, filed Jan. 13, 1999, which claims priority under 35 U.S.C. § 119 from GB Application No. 9801233.9, filed Jan. 21, 1998, and GB Application No. 9821517.1, filed Oct. 2, 1998.

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits $\alpha 1$ so exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen $\alpha$allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta \gamma 2/3$, $\alpha 2\beta \gamma 1$, $\alpha 5\beta 3\gamma 2/3$, $\alpha 6\beta \gamma 2$, $\alpha 6\beta \delta$ and $\alpha 4\beta \delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect.

Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta \gamma 2$ and $\alpha 3\beta \gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta \gamma 2$, $\alpha 2\beta \gamma 2$ or $\alpha 3\beta \gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors: containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolo-phthalazine ring system with any other functionality.

The present invention provides a class of triazolo-pyridazine derivatives which possess desirable binding properties at various $GABA_A$ receptor subtypes. The compounds in accordance with the present invention have good affinity as ligands for the α2 and/or α3 subunit of the human $GABA_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1-subunit are also encompassed within the scope of the present invention; such compounds will desirably exhibit functional selectivity in terms of a selective efficacy for the α2 and/or α3 subunit relative to the α1 subunit. Moreover, the compounds according to the present invention possess interesting pharmacokinetic properties, notably in terms of improved oral bioavailability.

The present invention provides a compound of formula I, or a pharmaceutically acceptable salt thereof:

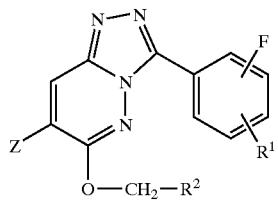

wherein

Z represents trifluoromethyl, 2-methylpropyl, 2,2-dimethylpropyl, 3-methylbutyl, 1-fluorobut-3-enyl, cyclobutyl, 1-methylcyclobutyl, 1-fluorocyclobutyl, 3-fluorocyclobutyl, 3,3-difluorocyclobutyl, 3-hydroxycyclobutyl, 3-benzyloxycyclobutyl, 3-oxocyclobutyl, 1-methylcyclohexyl, 4,4-difluoro-1-methylcyclohexyl, cyclopentylmethyl, 4-fluorocyclohex-3-enyl, 3-fluorophenyl, tetrahydrofur-2-yl, pyrrolidin-1-yl, 4-methyltetrahydropyran-4-yl or thien-2-yl;

$R^1$ represents hydrogen or fluoro; and $R^2$ represents methyl-isoxazolyl, methyl-pyrazolyl, methyl-imidazolyl, benzimidazolyl or methyl-triazolyl;

provided that, when Z represents 1-methylcyclobutyl, $R^1$ is hydrogen and $R^2$ represents 1-methyl-1H-1,2,4-triazol-3-yl or 2-methyl-2H-1,2,4-triazol-3-yl, then the fluorine atom is not at the 2-position of the phenyl ring.

Certain compounds in accordance with the present invention are encompassed within the generic scope of co-pending International Patent Application No. PCT/GB97/01946, published on Feb. 5, 1998 as WO 98/04559. There is, however, no specific disclosure therein of compounds corresponding to those of formula I as defined above.

The present invention also provides a compound of formula I as depicted above, or a pharmaceutically acceptable salt thereof, wherein Z represents trifluoromethyl, 2-methylpropyl, 2,2-dimethylpropyl, 3-methylbutyl, 1-fluorobut-3-enyl, cyclobutyl, 1-methylcyclobutyl, 1-fluorocyclobutyl, 3-fluorocyclobutyl, 3-hydroxycyclobutyl, 3-benzyloxycyclobutyl, 1-methylcyclohexyl, cyclopentylmethyl, pyrrolidin-1-yl or thien-2-yl; and $R^1$ and $R^2$ are as defined above; provided that, when Z represents 1-methylcyclobutyl, $R^1$ is hydrogen and $R^2$ represents 1-methyl-1H-1,2,4-triazol-3-yl or 2-methyl-2H-1,2,4-triazol-3-yl, then the fluorine atom is not at the 2-position of the phenyl ring.

The present invention further provides a compound of formula I as depicted above, or a pharmaceutically acceptable salt thereof, wherein Z represents cyclobutyl, 1-methylcyclobutyl, 1-fluorocyclobutyl, 1-methylcyclohexyl, pyrrolidin-1-yl or thien-2-yl; and $R^1$ and $R^2$ are as defined above;

provided that, when Z represents 1-methylcyclobutyl, $R^1$ is hydrogen and $R^2$ represents 1-methyl-1H-1,2,4-triazol-3-yl or 2-methyl-2H-1,2,4-triazol-3-yl, then the fluorine atom is not at the 2-position of the phenyl ring.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In the compounds of formula I above, the moiety Z suitably represents cyclobutyl.

The substituent $R^2$ suitably represents a ring of structure (a), (b), (c), (d), (e), (f) or (g):

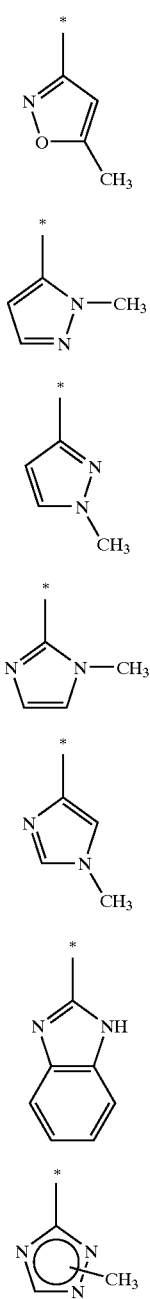

where the asterisk * denotes the point of attachment of the ring to the remainder of the molecule.

A particular moiety $R^2$ is represented by the structure (g) as depicted above.

Where permissible, the compounds of formula I as defined above suitably possess a fluorine atom at the 2-position of the phenyl ring.

A particular sub-class of compounds according to the invention is represented by the compounds of formula IIA, and pharmaceutically acceptable salts thereof.

(IIA)

wherein $R^1$ is as defined above; and
$R^3$ represents hydrogen or fluoro.
Suitably, $R^3$ represents hydrogen.

A particular subset of the compounds of formula IIA above is represented by the compounds of formula IIB, and pharmaceutically acceptable salts thereof:

(IIB)

wherein $R^1$ and $R^3$ are as defined above.

Specific compounds within the scope of the present invention include:

7-cyclobutyl-3-(2-fluorophenyl)-6-(2-methyl-2H-1,2,4-triazol-3-ylmethoxy)-1,2,4-triazolo[4,3-b]pyridazine;
7-cyclobutyl-3-(2-fluorophenyl)-6-(1-methyl-1H-1,2,4-triazol-3-ylmethoxy)-1,2,4-triazolo[4,3-b]pyridazine;
7-cyclobutyl-3-(3-fluorophenyl)-6-(2-methyl-2H-1,2,4-triazol-3-ylmethoxy)-1,2,4-triazolo[4,3-b]pyridazine;
7-cyclobutyl-3-(4-fluorophenyl)-6-(2-methyl-2H-1,2,4-triazol-3-ylmethoxy)-1,2,4-triazolo[4,3-b]pyridazine;
7-cyclobutyl-3-(2,4-difluorophenyl)-6-(2-methyl-2H-1,2,4-triazol-3-ylmethoxy)-1,2,4-triazolo[4,3-b]pyridazine;
7-cyclobutyl-3-(3,5-difluorophenyl)-6-(2-methyl-2H-1,2,4-triazol-3-ylmethoxy)-1,2,4-triazolo[4,3-b]pyridazine;
3-(2,4-difluorophenyl)-7-(1-methylcyclobutyl)-6-(2-methyl-2H-1,2,4-triazol-3-ylmethoxy)-1,2,4-triazolo[4,3-b]pyridazine;
7-cyclobutyl-3-(3,4-difluorophenyl)-6-(2-methyl-2H-1,2,4-triazol-3-ylmethoxy)-1,2,4-triazolo[4,3-b]pyridazine;
7-cyclobutyl-3-(2,3-difluorophenyl)-6-(2-methyl-2H-1,2,4-triazol-3-ylmethoxy)-1,2,4-triazolo[4,3-b ]pyridazine;
7-cyclobutyl-3-(2,6-difluorophenyl)-6-(2-methyl-2H-1,2,4-triazol-3-ylmethoxy)-1,2,4-triazolo[4,3-b]pyridazine;
7-cyclobutyl-3-(2,5-difluorophenyl)-6-(2-methyl-2H-1,2,4-triazol-3-ylmethoxy)-1,2,4-triazolo[4,3-b]pyridazine;
3-(2,4-difluorophenyl)-7-(1-methylcyclohexyl)-6-(2-methyl-2H-1,2,4-triazol-3-ylmethoxy)-1,2,4-triazolo[4,3-b]pyridazine;

3-(2,4-difluorophenyl)-7-(1-methylcyclohexyl)-6-(1-methyl-1H-1,2,4-triazol-3-ylmethoxy)-1,2,4-triazolo[4,3-b]pyridazine;
7-cyclobutyl-3-(2-fluorophenyl)-6-(1-methyl-1H-pyrazol-3-ylmethoxy)-1,2,4-triazolo[4,3-b]pyridazine;
7-cyclobutyl-3-(2-fluorophenyl)-6-(5-methylisoxazol-3-ylmethoxy)-1,2,4-triazolo[4,3-b]pyridazine;
7-cyclobutyl-3-(2-fluorophenyl)-6-(1-methyl-1H-imidazol 2-ylmethoxy)-1,2,4-triazolo[4,3-b]pyridazine;
7-cyclobutyl-3-(2-fluorophenyl)-6-(4-methyl-4H-1,2,4-triazol-3-ylmethoxy)-1,2,4-triazolo[4,3-b]pyridazine;
3-(2-fluorophenyl)-6-(2-methyl-2H-1,2,4-triazol-3-ylmethoxy)-7-(thien-2-yl)-1,2,4-triazolo[4,3-b]pyridazine;
3-(2,4-difluorophenyl)-6-(2-methyl-2H-1,2,4-triazol-3-ylmethoxy)-7-(thien-2-yl)-1,2,4-triazolo[4,3-b]pyridazine;
6-(1H-benzimidazol-2-ylmethoxy)-7-cyclobutyl-3-(2,4-difluorophenyl)-1,2,4-triazolo[4,3-b]pyridazine;
3-(2,4-difluorophenyl)-6-(2-methyl-2H-1,2,4-triazol-3-ylmethoxy)-7-(pyrrolidin-1-yl)-1,2,4-triazolo[4,3-b]pyridazine;
3-(2,4-difluorophenyl)-6-(1-methyl-1H-1,2,4-triazol-3-ylmethoxy)-7-(pyrrolidin-1-yl)-1,2,4-triazolo[4,3-b]pyridazine;
3-(2-fluorophenyl)-6-(1-methyl-1H-1,2,4-triazol-3-ylmethoxy)-7-(pyrrolidin-1-yl)-1,2,4-triazolo [4,3-b]pyridazine;
7-cyclobutyl-3-(2-fluorophenyl)-6-(1-methyl-1H-imidazol-4-ylmethoxy)-1,2,4-triazolo[4,3-b]pyridazine;
7-(1-fluorocyclobutyl)-3-(2-fluorophenyl)-6-(2-methyl-2H-1,2,4-triazol-3-ylmethoxy)-1,2,4-triazolo [4,3-b]pyridazine;
7-cyclobutyl-3-(2-fluorophenyl)-6-(2-methyl-2H-pyrazol-3-ylmethoxy)-1,2,4-triazolo[4,3-b]pyridazine;
7-(2,2-dimethylpropyl)-3-(2-fluorophenyl)-6-(2-methyl-2H-1,2,4-triazol-3-ylmethoxy)-1,2,4-triazolo [4,3-b]pyridazine;
3-(2-fluorophenyl)-7-(2-methylpropyl)-6-(2-methyl-2H-1,2,4-triazol-3-ylmethoxy)-1,2,4-triazolo[4,3-b]pyridazine;
3-(2-fluorophenyl)-7-(3-methylbutyl)-6-(2-methyl-2H-1,2,4-triazol-3-ylmethoxy)-1,2,4-triazolo[4,3-b]pyridazine;
7-cyclopentylmethyl-3-(2-fluorophenyl)-6-(2-methyl-2H-1,2,4-triazol-3-ylmethoxy)-1,2,4-triazolo[4,3-b]pyridazine;
7-(3-benzyloxycyclobutyl)-3-(2-fluorophenyl)-6-(2-methyl-2H-1,2,4-triazol-3-ylmethoxy)-1,2,4-triazolo[4,3-b]pyridazine;
3-(2-fluorophenyl)-7-(3-hydroxycyclobutyl)-6-(2-methyl-2H-1,2,4-triazol-3-ylmethoxy)-1,2,4-triazolo[4,3-b]pyridazine;
7-(1-fluorobut-3-enyl)-3-(2-fluorophenyl)-6-(2-methyl-2H-1,2,4-triazol-3-ylmethoxy)-1,2,4-triazolo[4,3-b]pyridazine;
7-(3-fluorocyclobutyl)-3-(2-fluorophenyl)-6-(2-methyl-2H-1,2,4-triazol-3-ylmethoxy)-1,2,4-triazolo[4,3-b]pyridazine;
3-(2-fluorophenyl)-6-(2-methyl-2H-1,2,4-triazol-3-ylmethoxy)-7-trifluoromethyl-1,2,4-triazolo[4,3-b]pyridazine;
3-(2-fluorophenyl)-7-(4-methyltetrahydropyran-4-yl)-6-(2-methyl-2H-1,2,4-triazol-3-ylmethoxy)-1,2,4-triazolo[4,3-b]pyridazine;
3-(2-fluorophenyl)-7-(4-methyltetrahydropyran-4-yl)-6-(1-methyl-1H-1,2,4-triazol-3-ylmethoxy)-1,2,4-triazolo[4,3-b]pyridazine;
7-(4,4-difluoro-1-methylcyclohexyl)-3-(2-fluorophenyl)-6-(2-methyl-2H-1,2,4-triazol-3-ylmethoxy)-1,2,4-triazolo[4,3-b]pyridazine;
7-(4-fluoro-1-methylcyclohex-3-enyl)-3-(2-fluorophenyl)-6-(2-methyl-2H-1,2,4-triazol-3-ylmethoxy)-1,2,4-triazolo[4,3-b]pyridazine;
7-(4,4-difluoro-1-methylcyclohexyl)-3-(2-fluorophenyl)-6-(1-methyl-1H-1,2,4-triazol-3-ylmethoxy)-1,2,4-triazolo[4,3-b]pyridazine;
3-(2-fluorophenyl)-6-(2-methyl-2H-1,2,4-triazol-3-ylmethoxy)-7-(3-oxocyclobutyl)-1,2,4-triazolo [4,3-b]pyridazine;
7-(3,3-difluorocyclobutyl)-3-(2-fluorophenyl)-6-(2-methyl-2H-1,2,4-triazol-3-ylmethoxy)-1,2,4-triazolo[4,3-b]pyridazine;
3-(2-fluorophenyl)-6-(2-methyl-2H-1,2,4-triazol-3-ylmethoxy)-7-(tetrahydrofur-2-yl)-1,2,4-triazolo[4,3-b]pyridazine;
7-(3-fluorophenyl)-3-(2-fluorophenyl)-6-(2-methyl-2H-1,2,4-triazol-3-ylmethoxy)-1,2,4-triazolo[4,3-b]pyridazine;
and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

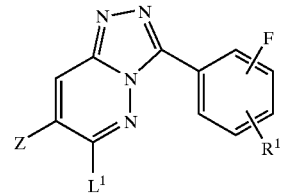

wherein Z, $R^1$ and $R^2$ are as defined above; and $L^1$ represents a suitable leaving group.

The leaving group $L^1$ is typically a halogen atom, especially chloro.

The reaction between compounds III and IV is conveniently effected by stirring the reactants in a suitable solvent, typically N,N-dimethyl-formamide or tetrahydrofuran, in the presence of a strong base such as sodium hydride, lithium bis(trimethylsilyl)amide or potassium bis(trimethylsilyl)amide.

The intermediates of formula III above may be prepared by reacting a compound of formula V with a substantially equimolar amount of a hydrazine derivative of formula VI:

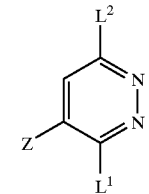

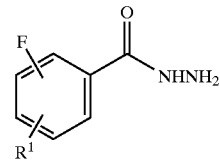

wherein Z, $R^1$ and $L^1$ are as defined above, and $L^2$ represents a suitable leaving group; followed, if necessary, by separation of the resulting mixture of isomers by conventional means.

The leaving group $L^2$ is typically a halogen atom, especially chloro. In the intermediates of formula V, the leaving groups $L^1$ and $L^2$ may be the same or different, but are suitably the same, preferably both chloro.

The reaction between compounds V and VI is conveniently effected by heating the reactants in the presence of a proton source such as triethylamine hydrochloride, typically at reflux in an inert solvent such as xylene or 1,4-dioxane.

Alternatively, the intermediates of formula III above may be prepared by reacting a hydrazine derivative of formula VII with an aldehyde derivative of formula VIII:

(VII)

[Structure VII: pyridazine with NHNH2, Z, and L¹ substituents]

(VIII)

[Structure VIII: fluorophenyl with CHO and R¹]

wherein Z, R¹ and L¹ are as defined above; followed by cyclization of the intermediate Schiff's base thereby obtained.

The reaction between compounds VII and VIII is conveniently effected under acidic conditions, for example in the presence of a mineral acid such as hydrochloric acid. Cyclization of the resulting Schiff's base intermediate may then conveniently be carried out by treatment with iron(III) chloride in a suitable solvent, e.g. an alcoholic solvent such as ethanol, at an elevated temperature, typically at a temperature in the region of 60–70° C.

The intermediates of formula VII above may be prepared by reacting the appropriate compound of formula V as defined above with hydrazine hydrate, typically in 1,4-dioxane at the reflux temperature of the solvent; followed, if necessary, by separation of the resulting mixture of isomers by conventional means.

In an alternative approach, the intermediates of formula III above may be prepared by reacting the hydrazine derivative of formula VII as defined above with a compound of formula IX:

(IX)

[Structure IX: fluorophenyl with Q and R¹]

wherein R¹ is as defined above, and Q represents a reactive carboxylate moiety; followed by cyclization of the hydrazide derivative of formula X thereby obtained:

(X)

[Structure X: pyridazine-NHNH-C(=O)-fluorophenyl with Z, L¹, R¹]

wherein Z, R¹ and L¹ are as defined above.

Suitable values for the reactive carboxylate moiety Q include esters, for example $C_{1-4}$ alkyl esters; acid anhydrides, for example mixed anhydrides with $C_{1-4}$ alkanoic acids; acid halides, for example acid chlorides; and acylimidazoles. Suitably, Q represents an acid chloride moiety.

The reaction between compounds VII and IX is conveniently effected under basic conditions, e.g. in the presence of triethylamine, suitably in an inert solvent such as diethyl ether, and typically at a temperature in the region of 0° C. Cyclization of the resulting compound of formula X may then conveniently be carried out by treatment with 1,2-dibromo-1,1,2,2-tetrachloroethane and triphenylphosphine, in the presence of a base such as triethylamine, suitably in an inert solvent such as acetonitrile, and typically at a temperature in the region of 0° C.

The reaction between compound V and hydrazine hydrate or compound VI will, as indicated above, usually give rise to a mixture of isomeric products depending upon whether the hydrazine nitrogen atom displaces the leaving group $L^1$ or $L^2$. Thus, in addition to the required product of formula III, the isomeric compound wherein the moiety Z is attached at the 8-position will usually be obtained to some extent; and likewise for compound VII. For this reason it will generally be necessary to separate the resulting mixture of isomers by conventional methods such as chromatography.

In another procedure, the compounds of formula I as defined above may be prepared by a process which comprises reacting a compound of formula XI (or its 1,2,4-triazolo[4,3-b]pyridazin-6-one tautomer) with a compound of formula XII:

(XI)

[Structure XI: triazolopyridazine with Z, OH, and fluorophenyl-R¹]

(XII)

$R^2-CH_2-L^3$ wherein Z, R¹ and R² are as defined above, and L³ represents a suitable leaving group.

The leaving group $L^3$ is suitably a halogen atom, typically chloro or bromo.

The reaction between compounds XI and XII is conveniently effected by stirring the reactants in a suitable solvent, typically N,N-dimethylformamide, in the presence of a strong base such as sodium hydride.

The intermediates of formula XI above may conveniently be prepared by reacting a compound of formula III as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compounds of formula I as defined above may be prepared by a process which comprises reacting a compound of formula Z—CO₂H with a compound of formula XIII:

(XIII)

[Structure XIII: triazolopyridazine with O-CH₂-R², and fluorophenyl-R¹]

wherein Z, R¹ and R² are as defined above; in the presence of silver nitrate and ammonium persulphate.

The reaction is conveniently carried out in a suitable solvent, for example water or aqueous acetonitrile, optionally under acidic conditions, e.g. using sulphuric acid, typically at an elevated temperature.

The intermediates of formula XIII correspond to the compounds of formula I as defined above wherein Z is hydrogen, and they may therefore be prepared by methods analogous to those described above for preparing the corresponding compounds of formula I.

In a still further procedure, the compounds of formula I as defined above may be prepared by a process which comprises reacting a compound of formula XIV with a compound of formula XV:

(XIV)

(XV)

wherein Z, $R^1$ and $R^2$ are as defined above, M represents —$B(OH)_2$ or —$Sn(Alk)_3$ in which Alk represents a $C_{1-6}$ alkyl group, typically n-butyl, and $L^4$ represents a suitable leaving group; in the presence of a transition metal catalyst.

The leaving group $L^4$ is suitably a halogen atom, e.g. bromo.

A suitable transition metal catalyst of use in the reaction between compounds XIV and XV comprises dichlorobis(triphenylphosphine)-palladium(II) or tetrakis(triphenylphosphine)palladium(0).

The reaction between compounds XIV and XV is conveniently effected in an inert solvent such as N,N-dimethylformamide, typically at an elevated temperature.

The intermediates of formula XIV may be prepared by reacting a compound of formula IV as defined above with a compound of-formula XVI:

(XVI)

wherein Z, $L^1$ and $L^4$ are as defined above; under conditions analogous to those described above for the reaction between compounds III and IV.

In a yet further procedure, the compounds of formula I wherein Z represents 1-fluorocyclobutyl may be prepared by a process which comprises reacting a compound of formula XVII:

(XVII)

wherein $R^1$ and $R^2$ are as defined above; with a fluorinating agent.

Similarly, the compounds of formula I wherein Z represents 3-fluorocyclobutyl, or 1-fluorobut-3-enyl, or a mixture thereof, may be prepared by a process which comprises reacting a compound of formula XVIII:

(XVIII)

wherein $R^1$ and $R^2$ are as defined above; with a fluorinating agent. Where a mixture of products is obtained, the individual components thereof may be isolated by conventional means including chromatography.

Similarly, the compounds of formula I wherein Z represents 3,3-difluorocyclobutyl may be prepared by a process which comprises reacting the corresponding compound wherein Z represents 3-oxocyclobutyl with a fluorinating agent.

A suitable fluorinating agent for use in the above reactions is diethylaminosulphur trifluoride (DAST), in which case the reaction can conveniently be brought about by stirring the reactants in an inert solvent such as dichloromethane, typically at a temperature in the region of −78° C.

The intermediates of formula XVII may be prepared by reacting a compound of formula IV as defined above with a compound of formula XIX:

(XIX)

wherein $R^1$ and $L^1$ are as defined above; under conditions analogous to those described above for the reaction between compounds III and IV.

The intermediates of formula XIX may in turn be prepared by reacting cyclobutanone with a compound of formula XX:

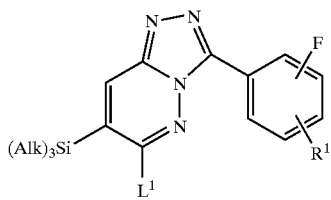

(XX)

wherein $R^1$ and $L^1$ are as defined above, and Alk represents $C_{1-6}$ alkyl, typically methyl.

The reaction is conveniently effected by treating the reagents with a fluoride source, e.g. a catalytic quantity of tetrabutylammonium difluorotriphenylstannate, suitably in an inert solvent such as tetrahydrofuran.

The intermediates of formula XX correspond to the compounds of formula III as defined above wherein Z is —Si(Alk)$_3$, and they may therefore be prepared by methods analogous to those described above for preparing the corresponding compounds of formula III.

The compounds of formula XVIII above (corresponding to compounds of formula I wherein Z represents 3-hydroxycyclobutyl) may be prepared by hydrogenolysis of a compound of formula XXI:

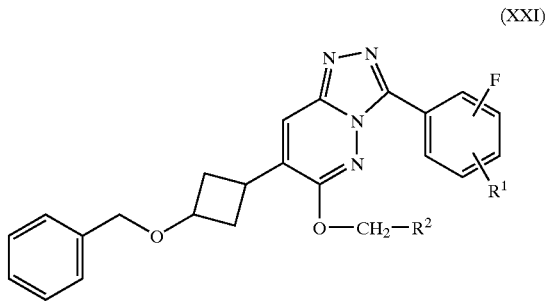

(XXI)

wherein $R^1$ and $R^2$ are as defined above.

The reaction is conveniently effected by transfer hydrogenation, which comprises contacting compound XXI with a hydrogenation catalyst in the presence of a hydrogen donor. A suitable hydrogenation catalyst is palladium on carbon, ideally 10% palladium on carbon. A suitable hydrogen donor is ammonium formate, in which case the reaction is advantageously performed in formic acid.

In an additional procedure, the compounds of formula I as defined above may be prepared by a process which comprises reacting a compound of formula XXII with a compound of formula XXIII:

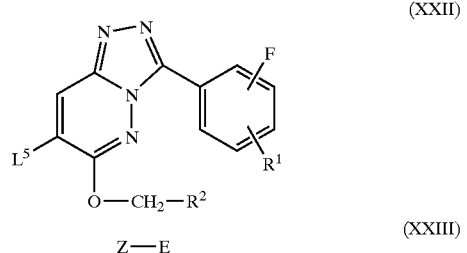

(XXII)

Z—E (XXIII)

wherein Z, $R^1$ and $R^2$ are as defined above, $L^5$ represents a suitable leaving group, and E represents —B(OH)$_2$ or the residue of an organozinc reagent; in the presence of a transition metal catalyst.

The leaving group $L^5$ is suitably a halogen atom, e.g. bromo or iodo.

Where E represents —B(OH)$_2$, the transition metal catalyst of use in the reaction between compounds XXII and XXIII is suitably tetrakis(triphenylphosphine)palladium(0), and the reaction is conveniently effected at an elevated temperature in the presence of potassium phosphate and a solvent such as N,N-dimethylformamide.

Where E represents the residue of an organozinc reagent, the intermediate XXIII is suitably prepared by reacting an iodide derivative Z—I with zinc dust, typically in the presence of 1,2-dibromoethane and a solvent such as N,N-dimethylformamide. In this instance, the transition metal catalyst of use in the reaction between compounds XXII and XXIII is ideally tris(dibenzylideneacetone)dipalladium(0), and the reaction is conveniently effected in the presence of tri-2-furylphosphine and a solvent such as N,N-dimethylformamide.

The compounds of formula XXI above (corresponding to compounds of formula I wherein Z represents 3-benzyloxycyclobutyl) may be similarly prepared by reacting a compound of formula XXII as defined above with a compound of formula XXIV:

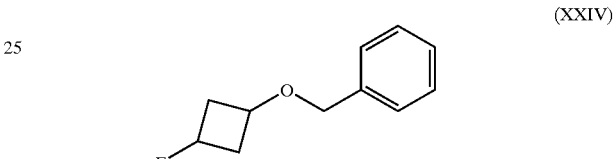

(XXIV)

wherein E is as defined above; in the presence of a transition metal catalyst; under conditions analogous to those described above for the reaction between compounds XXII and XXIII.

The intermediates of formula XXII may be prepared by reacting a compound of formula IV as defined above with a compound of formula XXV:

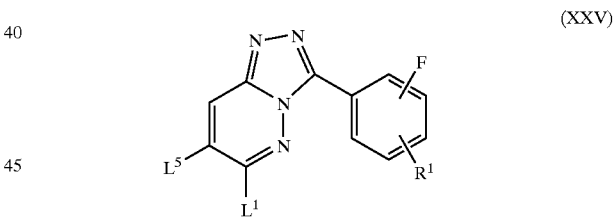

(XXV)

wherein $R^1$, $L^1$ and $L_5$ are as defined above; under conditions analogous to those described above for the reaction between compounds III and IV.

The intermediates of formula XXV may suitably be prepared by treatment of the appropriate precursor of formula XX as defined above with a fluoride source, e.g. tetrabutylammonium difluorotriphenylstannate or tris(dimethylamino)sulphur (trimethyl)difluoride, in the presence of an $L^5$-containing reagent, e.g. 1,2-dibromotetrafluoroethane or 1,2-diiodoethane.

The compounds of formula I as defined above wherein Z represents trifluoromethyl may be prepared by a process which comprises reacting a compound of formula XXII as defined above with iodotrifluoromethane.

The reaction is suitably performed in the presence of copper powder, typically in a sealed tube at an elevated temperature, e.g. a temperature in the region of 80° C.

The intermediates of formula IV above may be prepared by the procedures described in EP-A-0421210, or by methods analogous thereto.

Where they are not commercially available, the starting materials of formula V, VI, VIII, IX, XII, XV, XVI and XXIV may be prepared by methods analogous to those described in the accompanying Examples, or by standard methods well known from the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for (α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

7-Cyclobutyl-3-(2-fluorophenyl)-6-(2-methyl-2H-1, 2,4-triazol-3-ylmethoxy)-1,2,4-triazolo[4,3-b] pyridazine a) 3,6-Dichloro-4-cyclobutylpyridazine Concentrated sulphuric acid (53.6 ml, 1.0 mol) was added carefully to a stirred suspension of 3,6-dichloropyridazine (50.0 g, 0.34 mol) in water (1.25 l). This mixture was then heated to 70° C. (internal temperature) before the addition of cyclobutane carboxylic acid (35.3 ml, 0.37 mol). A solution of silver nitrate (11.4 g, 0.07 mol) in water (20 ml) was then added over approximately one minute. This caused the reaction mixture to become milky in appearance. A solution of ammonium persulphate (230 g, 1.0 mol) in water (0.63 l) was then added over 20–30 minutes. The internal temperature rose to approximately 85° C. During the addition the product formed as a sticky precipitate. Upon complete addition the reaction was stirred for an additional 5 minutes, then allowed to cool to room temperature. The mixture was then poured onto ice and basified with concentrated aqueous ammonia, with the addition of more ice as required to keep the temperature below 10° C. The aqueous was extracted with dichloromethane (×3). The combined extracts were dried ($MgSO_4$), filtered and evaporated to give the title compound (55.7 g, 82%) as an oil. $^1$H nmr ($CDCl_3$) indicated contamination with approximately 5% of the 4,5-dicyclobutyl compound. However, this material was used without further purification. Data for the title compound: $^1$H NMR (360 MHz, $d_6$-DMSO) δ 1.79–1.90 (1H, m), 2.00–2.09 (1H, m), 2.18–2.30 (2H, m), 2.33–2.40 (2H, m), 3.63–3.72 (1H, m), 7.95 (1H, s); MS (ES$^+$) m/e 203 [MH]$^+$, 205 [MH]$^+$, 207 [MH]$^+$.

b) 6-Chloro-7-cyclobutyl-3-(2-fluorophenyl)-1,2,4-triazolo [4,3-b]pyridazine

A mixture of 3,6-dichloro-4-cyclobutylpyridazine from above (3.0 g, 14.7 mmol), 2-fluorobenzhydrazide (3.0 g, 19.5 mmol) and triethylamine hydrochloride (3.0 g, 21.8 mmol) in p-xylene (50 ml) was stirred and heated at reflux under a stream of nitrogen for 20 hours. Upon cooling the volatiles were removed in vacuo. The residue was partitioned between dichloromethane and water. The aqueous was basified by the addition of solid potassium carbonate. Some dark insoluble material was removed by filtration at this stage. The aqueous was further extracted with dichloromethane (×2). The combined extracts were dried ($MgSO_4$), filtered and evaporated. The residue was purified by chromatography on silica gel eluting with 20%→30% ethyl acetate/dichloromethane to give the title compound (2.2 g, 49%) as a light-brown solid. Data for the title compound: $^1$H NMR (250 MHz, $CDCl_3$) δ 1.85–2.08 (1H, m), 2.08–2.30 (3H, m), 2.38–2.64 (2H, m), 3.62–3.84 (1H, m), 7.19–7.46 (2H, m), 7.46–7.67 (1H, m), 7.80–7.96 (1H, m), 7.99 (1H, s), MS (ES$^+$) m/e 303 [MH]$^+$, 305 [MH]$^+$.

c) 7-Cyclobutyl-3-(2-fluorophenyl)-6-(2-methyl-2H-1,2,4-triazol-3-ylmethoxy)-1,2,4-triazolo[4,3-b]pyridazine To a solution of (2-methyl-2H-1,2,4-triazol-3-yl) methanol (0.123 g, 1.09 mmol) (prepared using the conditions described in EP-A-421210) in DMF (15 ml) was added sodium hydride (0.044 g of a 60% dispersion in oil, 1.1 mol eq.) and the reaction mixture was stirred at room temperature for 30 minutes. After this time the foregoing product (0.3 g, 0.99 mmol) was added as a solution in DMF (15 ml) and the reaction mixture was stirred at room temperature for 2 hours. The reaction mixture was diluted with water (100 ml) and the aqueous extracted with dichloromethane (4×100 ml). The combined extracts were dried ($Na_2SO_4$), filtered and evaporated. The residue was purified by chromatography on silica gel using 2% MeOH in dichloromethane as eluent to give the required product (0.294 g, 78%). $^1$H NMR (250 MHz, $CDCl_3$) δ 1.82–2.00 (1H, m), 2.00–2.26 (3H, m), 2.26–2.48 (2H, m), 3.53–3.70 (1H, m), 3.84 (3H, s), 5.47 (2H, s), 7.22–7.42 (2H, m), 7.50–7.64 (1H, m), 7.76–7.96

(3H, m); MS (ES$^+$) m/e 380 [MH]$^+$. Anal. Found C, 60.21; H, 4.77; N, 25.66%. $C_{19}H_{18}FN_7O$ requires C, 60.15; H, 4.78; N, 25.84%.

EXAMPLE 2

7-Cyclobutyl-3-(2-fluorophenyl)-6-(1-methyl-1H-1, 2,4-triazol-3-ylmethoxy-1,2,4-triazolo[4,3-b] pyridazine This compound was prepared using the procedures described in Example 1 Steps a), b) and c) with (1-methyl-1H-1,2,4-triazol-3-yl)-methanol (prepared using the conditions described in EP-A-421210) used instead of (2-methyl-2H-1,2,4-triazol-3-yl)methanol in Step c). Data for the title compound: $^1$H NMR (360 MHz, d$_6$-DMSO) δ 1.74–1.87 (1H, m), 1.94–2.08 (1H, m), 2.14–2.34 (4H, m), 3.50–3.64 (1H, m), 3.87 (3H, s), 5.30 (2H, s), 7.41–7.51 (2H, m), 7.62–7.70 (1H, m), 7.96–8.03 (1H, m), 8.14 (1H, s), 8.50 (1H, s); MS (ES$^+$) m/e 380 [MH]$^+$.

EXAMPLE 3

7-Cyclobutyl-3-(3-fluorophenyl)-6-(2-methyl-2H-1, 2,4-triazol-3-ylmethoxy)-1,2,4-triazolo[4,3-b] pyridazine This compound was prepared using the procedures described in Example 1 Steps a), b) and c) using 3-fluorobenzhydrazide instead of 2-fluorobenzhydrazide in Step b). Data for the title compound: $^1$H NMR (250 MHz, d$_6$-DMSO) δ 1.74–1.90 (1H, m), 1.94–2.12 (1H, m), 2.12–2.36 (4H, m), 3.51–3.69 (1H, m), 3.93 (3H, s), 5.70 (2H, s), 7.36–7.47 (1H, m), 7.62–7.72 (1H, m), 8.00 (1H, s), 8.14–8.32 (3H, m); MS (ES$^+$) m/e 380 [MH]$^+$.

EXAMPLE 4

7-Cyclobutyl-3-(4-fluorophenyl)-6-(2-methyl-2H-1, 2,4-triazol-3-ylmethoxy)-1,2,4-triazolo[4,3-b] pyridazine This compound was prepared using the procedures described in Example 1 Steps a), b) and c) using 4-fluorobenzhydrazide instead of 2-fluorobenzhydrazide in Step b). Data for the title compound: $^1$H NMR (250 MHz, d$_6$-DMSO) δ 1.98–2.12 (1H, m), 2.18–2.32 (1H, m), 2.32–2.55 (4H, m), 3.72–3.90 (1H, m), 4.17 (3H, s), 5.90 (2H, s), 7.62–7.76 (2H, m), 8.27 (1H, s), 8.40 (1H, s), 8.64–8.74 (2H, m); MS (ES$^+$) m/e 380 [MH]$^+$.

EXAMPLE 5

7-Cyclobutyl-3-(2,4-difluorophenyl)-6-(2-methyl-2H-1,2,4-triazol-3-ylmethoxy)-1,2,4-triazolo [4,3-b] pyridazine This compound was prepared using the procedures described in Example 1 Steps a), b) and c) using 2,4-difluorobenzhydrazide instead of 2-fluorobenzhydrazide in Step b). Data for the title compound: $^1$H NMR (250 MHz, d$_6$-DMSO) δ 1.72–1.90 (1H, m), 1.90–2.12 (1H, m), 2.12–2.36 (4H, m), 3.50–3.68 (1H, m), 3.82 (3H, s), 5.50 (2H, s), 7.30–7.42 (1H, m), 7.52–7.64 (1H, m), 7.93–8.12 (2H, m), 8.20 (1H, s); MS (ES$^+$) m/e 398 [MH]$^+$.

EXAMPLE 6

7-Cyclobutyl-3-(3,5-difluorophenyl)-6-(2-methyl-2H-1,2,4-triazol-3-ylmethoxy)-1,2,4-triazolo[4,3-b] pyridazine a) 3-Chloro-4-cyclobutyl-6-hydrazinopyridazine 3,6-Dichloro-4-cyclobutylpyridazine (10 g, 0.049 mol) and hydrazine hydrate (14 ml, 0.30 mol) were heated at reflux in dioxan (125 ml) for 24 hours. Upon cooling the desired isomer crystallized from the reaction and was collected by filtration (4.8 g, 49%). $^1$H NMR (250 MHz, d$_6$-DMSO) δ 1.68–1.86 (1H, m), 2.00–2.11 (3H, m), 2.29–2.38 (2H, m), 3.52–3.61 (1H, m), 4.35 (2H, br), 6.99 (1H, s), 8.06 (1H, br); MS (ES$^+$) m/e 198 [MH]$^+$, 200 [MH]$^+$.

b) N-(6-chloro-5-cyclobutylpyridazin-3-yl)-N'-(3,5-difluoro-benzylidene)hydrazine 3-Chloro-4-cyclobutyl-6-hydrazinopyridazine (0.502 g, 2.53 mmol) and 3,5-difluorobenzaldehyde (285 ml, 2.78 mmol) were stirred in 0.2M hydrochloric acid (10 ml) for 2 hours. This product was then collected by filtration and dried (0.81 g, 99%). MS (ES$^+$) 323 [MH]$^+$, 325 [MH]$^+$.

c) 6-Chloro-7-cyclobutyl-3-(3,5-difluorophenyl)-1,2,4-triazolo[4,3-b]pyridazine

Ferric chloride (3.423 g, 12.66 mmol) in ethanol (15 ml) was added dropwise to a solution of N-(6-chloro-5-cyclobutylpyridazin-3-yl)-N'-(3,5-difluorobenzylidene) hydrazine (0.816 g, 2.53 mmol) in ethanol (35 ml) and heated at 70° C. After 3 hours the reaction mixture was partitioned between dichloromethane (250 ml) and brine (250 ml). The organic phase was dried (MgSO$_4$), filtered and evaporated. The residue was purified by chromatography on silica gel, eluting with ethyl acetate-hexane mixtures to afford the title pyridazine (0.51 g, 63%). $^1$H NMR (250 MHz, CDCl$_3$) 1.84–2.08 (1H, m), 2.08–2.36 (3H, m), 2.42–2.68 (2H, m), 3.65–3.87 (1H, m), 6.88–7.06 (1H, m), 8.01 (1H, s), 8.04–8.21 (2H, m). MS (ES$^+$) 321 [MH]$^+$, 323 [MH]$^+$.

d) 7-Cyclobutyl-3-(3,5-difluorophenyl)-6-(2-methyl-2H-1, 2,4-triazol-3-ylmethoxy)-1,2,4-triazolo[4,3-b]pyridazine To a solution of (2-methyl-2H-1,2,4-triazol-3-yl) methanol (0.099 g, 0.879 mmol) (prepared using the conditions described in EP-A-421210) in DMF (15 ml) was added sodium hydride (0.035 g of a 60% dispersion in oil, 1.1 mol eq.) and the reaction mixture was stirred at room temperature for 30 minutes. After this time the foregoing product (0.256 g, 0.799 mmol) was added as a solution in DMF (15 ml) and the reaction mixture was stirred at room temperature for 2 hours. The reaction mixture was diluted with water (100 ml) and the aqueous extracted with dichloromethane (4×100 ml). The combined extracts were dried (Na$_2$SO$_4$), filtered and evaporated. The residue was purified by chromatography on silica gel using 3% MeOH in dichloromethane as eluent to give the required product (0.120 g, 38%). $^1$H NMR (360 MHz, CDCl$_3$) δ 1.86–2.02 (1H, m), 2.08–2.25 (3H, m), 2.32–2.46 (2H, m), 3.56–3.70 (1H, m), 4.01 (3H, s), 5.64 (2H, s), 6.92–7.01 (1H, m), 7.90 (1H, s), 7.94 (1H, s), 8.03–8.12 (2H, m); MS (ES$^+$) m/e 398 [MH]$^+$.

EXAMPLE 7

3-(2,4-Difluorophenyl)-7-(1-methylcyclobutyl)-6-(2-methyl-2H-1,2,4-triazol-3-ylmethoxy)-1,2,4-triazolo [4,3-b]pyridazine This compound was prepared using the procedures described in Example 1 Step a), using 1-methylcyclobutane carboxylic acid (*Journal of Organoinetallic Chemistry*, 1988, 352, 263–272) instead of cyclobutane carboxylic acid, and Example 6 Steps a), b), c) and d), using 2,4-difluorobenzaldehyde instead of 3,5-difluorobenzaldehyde in Step b): Data for the title compound: $^1$H NMR (360 MHz, CDCl$_3$) δ 1.52 (3H, s), 1.78–1.92 (1H, m), 2.04–2.26 (3H, m), 2.34–2.46 (2H, m), 3.88 (3H, s), 5.47 (2H, s), 7.00–7.15 (2H, m), 7.74 (1H, s) 7.83–7.93 (2H, m); MS (ES$^+$) m/e 412 [MH]$^+$.

EXAMPLE 8

7-Cyclobutyl-3-(3,4-difluorophenyl)-6-(2-methyl-2H-1,2,4-triazol-3-ylmethoxy)-1,2,4-triazolo [4,3-b] pyridazine This compound was prepared using the procedures described in Example 1 Step a) and Example 6 Steps a), b), c) and d), using 3,4-difluorobenzaldehyde instead of 3,5-difluorobenzaldehyde in Step b). Data for the title compound: $^1$H NMR (360 MHz, CDCl$_3$) δ 1.86–2.00 (1H, m), 2.06–2.24 (3H, m), 2.30–2.46 (2H, m), 3.57–3.70 (1H, m), 4.00 (3H, s), 5.62 (2H, s), 7.32–7.40 (1H, m), 7.90 (1H, s), 7.96 (1H, s), 8.20–8.80 (1H, m), 8.32–8.40 (1H, m); MS (ES$^+$) m/e 398 [MH]$^+$.

EXAMPLE 9

7-Cyclobutyl-3-(2,3-difluorophenyl)-6-(2-methyl-2H-1,2,4-triazol-3-ylmethoxy)-1,2,4-triazolo[4,3-b] pyridazine This compound was prepared using the procedures described in Example 1 Step a) and Example 6-Steps a), b), c) and d), using 2,3-difluorobenzaldehyde instead of 3,5-difluorobenzaldehyde in Step b). Data for the title compound: $^1$H NMR (360 MHz, CDCl$_3$) δ 1.86–1.98 (1H, m), 2.04–2.24 (3H, m), 2.30–2.44 (2H, m), 3.58–3.70 (1H, m), 3.90 (3H, s), 5.50 (2H, s), 7.26–7.34 (1H, m), 7.34–7.46 (1H, m), 7.62–7.80 (1H, m), 7.88 (1H, s), 7.92 (1H, s); MS (ES$^+$) m/e 398 [MH]$^+$.

EXAMPLE 10

7-Cyclobutyl-3-(2,6-difluorophenyl)-6-(2-methyl-2H-1,2,4-triazol-3-ylmethoxy)-1,2,4-triazolo[4,3-b] pyridazine This compound was prepared using the procedures described in Example 1 Step a) and Example 6 Steps a), b), c) and d), using 2,6-difluorobenzaldehyde instead of 3,5-difluorobenzaldehyde in Step b). Data for the title compound: $^1$H NMR (360 MHz, CDCl$_3$) δ 1.86–1.96 (1H, m), 2.04–2.24 (3H, m), 2.30–2.42 (2H, m), 3.56–3.68 (1H, m), 3.84 (3H, s), 5.42 (2H, s), 7.08–7.16 (2H, m), 7.55–7.60 (1H, m), 7.88 (2H, m); MS (ES$^+$) m/e 398 [MH]$^+$.

EXAMPLE 11

7-Cyclobutyl-3-(2,5-difluorophenyl)-6-(2-methyl-2H-1,2,4-triazol-3-ylmethoxy)-1,2,4-triazolo[4,3-b] pyridazine This compound was prepared using the procedures described in Example 1 Step a) and Example 6 Steps a), b), c) and d), using 2,5-difluorobenzaldehyde instead of 3,5-difluorobenzaldehyde in Step b). Data for the title compound: $^1$H NMR (360 MHz, CDCl$_3$) δ 1.86–1.98 (1H, m), 2.04–2.24 (3H, m), 2.30–2.46 (2H, m), 3.56–3.70 (1H, m), 3.90 (3H, s), 5.48 (2H, s), 7.20–7.30 (2H, m), 7.60–7.68 (1H, m), 7.88 (1H, s), 7.92 (1H, s); MS (ES$^+$) m/e 398 [MH]$^+$.

EXAMPLE 12

3-(2,4-Difluorophenyl)-7-(1-methylcyclohexyl)-6-(2-methyl-2H-1,2,4-triazol-3-ylmethoxy)-1,2,4-triazolo[4,3-b]pyridazine a) 3,6-Dichloro-4-(1-methylcyclohexyl)pyridazine Concentrated sulphuric acid (10.7 ml, 0.2 mol) was added to a solution of 3,6-dichloropyridazine (10 g, 67 mmol) in water (250 ml). This mixture was heated to 70° C. before addition of 1-methylcyclohexane carboxylic acid (9.67 g, 68 mmol). Silver nitrate (2.3 g, 13.5 mmol) in water (5 ml) was then added over one minute followed by ammonium persulphate (45.6 g, 0.2 mol) in water (95 ml) added over 20 minutes. Upon complete addition, the reaction was stirred for an additional 5 minutes and then allowed to cool to room temperature. The mixture was cooled to 0° C. (ice/water bath) and basified with concentrated aqueous ammonia solution (internal temperature <10° C.). The aqueous phase was extracted with dichloromethane (3×350 ml) and the combined extracts washed with brine (350 ml), dried (MgSO$_4$), filtered and evaporated. The residue was purified by chromatography on silica using 0→5% ethyl acetate in dichloromethane as eluent to give the required product (5.93 g): $^1$H NMR (250 MHz, CDCl$_3$) δ 1.33–1.74 (6H, m), 1.43 (3H, s), 1.80–1.96 (2H, m), 1.97–2.12 (2H, m), 7.49 (1H, s); MS (ES$^+$) m/e 249 [MH]$^+$, 247 [MH]$^+$, 245 [MH]$^+$.

b) 6-Chloro-3-(2,4-difluorophenyl)-7-(1-methylcyclohexyl)-1,2,4-triazolo[4,3-b]pyridazine A mixture of 3,6-dichloro-4-(1-methylcyclohexyl) pyridazine (1.29 g, 5.27 mmol), 2,4-difluorobenzoic hydrazide (1.72 g, 10 mmol) and triethylamine hydrochloride (1.09 g, 7.9 mmol) in p-xylene (5 ml) was stirred and heated at reflux for 24 hours. Upon cooling, the volatiles were removed in vacuo and the residue was partitioned between dichloromethane (100 ml) and water (100 ml) and NaHCO$_3$ (100 ml). Undissolved solid was removed by filtration. The layers were separated and the aqueous was further extracted with dichloromethane (2×100 ml). The combined organic extracts were dried (MgSO$_4$), filtered and evaporated. The residue was purified by chromatography on silica eluting with 0%→25% ethyl acetate in dichloromethane to give the required product (0.74 g): $^1$H NMR (250 MHz, CDCl$_3$) δ 1.34–1.74 (6H, m), 1.50 (3H, s), 1.90–2.15 (4H, m), 7.01–7.14 (2H, m), 7.87–7.98 (1H, m), 8.18 (1H, s); MS (ES$^+$) m/e 365 [MH], 363 [MH]$^+$.

c) 3-(2,4-Difluorophenyl)-7-(1-methylcyclohexyl)-6-(2-methyl-2H-1,2,4-triazol-3-ylmethoxy)-1,2,4-triazolo[4,3-b]pyridazine Sodium hydride (60% dispersion in oil, 13 mg, 0.33 mmol) was added to a stirred solution of (2-methyl-2H-1,2,4-triazol-3-yl)methanol (prepared using the conditions described in EP-A-421210; 37 mg, 0.33 mmol) in anhydrous N,N-dimethylformamide (5 ml) at room temperature under nitrogen. This was stirred for 30 mins and 6-chloro-3-(2,4-difluorophenyl)-7-(1-methylcyclohexyl)-1,2,4-triazolo[4,3-b]pyridazine (100 mg, 0.275 mmol) in N,N-dimethylformamide (3 ml) was then added and the mixture stirred for a further 60 minutes. The reaction was quenched with water (20 ml) and stirred for an additional 60 minutes. The precipitated solid was collected by filtration and washed with water. The solid was dissolved in dichloromethane (20 ml), filtered and evaporated. The residue was recrystallised from ethyl acetate/hexane to give the title compound (38 mg): m.p.=196° C.; $^1$H NMR (360 MHz, CDCl$_3$) δ 1.32 (3H, s), 1.33–1.66 (6H, m), 1.72–1.81 (2H, m), 1.93–2.03 (2H, m), 3.87 (3H, s), 5.50 (2H, s), 7.00–7.14 (2H, m), 7.83–7.90 (1H, m), 7.91 (1H, s), 8.00 (1H, s); MS (ES$^+$) m/e 440 [MH]$^+$; Anal. Found: C, 59.74; H, 5.23; N, 22.10. C$_{22}$H$_{23}$F$_2$N$_7$O requires: C, 60.13; H, 5.27; N, 22.31%.

EXAMPLE 13

3-(2,4-Difluorophenyl)-7-(1-methylcyclohexyl)-6-(1-methyl-1H-1,2,4-triazol-3-ylmethoxy)-1,2,4-triazolo[4,3-b]pyridazine This compound was prepared using the procedure described in Example 12 Step c) with (1-methyl-1H-1,2,4- triazol-3-yl)methanol (prepared using the conditions described in EP-A-421210) instead of (2-methyl-2H-1,2,4-triazol-3-yl)methanol. Data for the title compound: m.p.= 156° C.; $^1$H NMR (360 MHz, CDCl$_3$) δ 1.36 (3H, s), 1.37–1.66 (6H, m), 1.74–1.84 (2H, m), 1.99–2.10 (2H, m), 3.93 (3H, s), 5.44 (2H, s), 6.99–7.11 (2H, m), 7.96 (1H, s), 7.97–8.03 (1H, m), 8;04 (1H, s); MS (ES$^+$) m/e 4,40 [MH]$^+$; Anal. Found: C, 60.48; H, 5.08; N, 22.39. C$_{22}$H$_{23}$F$_2$N$_7$O requires: C, 60.13; H, 5.27; N, 22.31%.

EXAMPLE 14

7-Cyclobutyl-3-(2-fluorophenyl)-6-(1-methyl-1H-pyrazol-3-ylmethoxy)-1,2,4-triazolo[4,3-b]pyridazine This compound was prepared using the procedure described in Example 1 Step c) with (1-methyl-1H-pyrazol-3-yl)methanol (prepared using the conditions described in EP-A-91130) used instead of (2-methyl-2H-1,2,4-triazol-3-yl)methanol. Data for the title compound: m.p.=184–186° C.; $^1$H NMR (360 MHz, DMSO) δ 1.80 (1H, m), 1.99 (1H, m), 2.18 (4H, m), 3.55 (1H, m), 3.82 (3H, s), 5.23 (2H, s), 6.25 (1H, s), 7.44–7.51 (2H, m), 7.65 (2H, m), 7.99 (1H, m), 8.18 (1H, s); MS (ES$^+$) m/e 379 [MH]$^+$. Anal. Found C, 62.81; H, 4.69; N, 21.68. C$_{20}$H$_{19}$FN$_6$O. 0.2H$_2$O requires C, 62.88; H, 5.12; N, 22.00%.

EXAMPLE 15

7-Cyclobutyl-3-(2-fluorophenyl)-6-(5-methylisoxazol-3-ylmethoxy)-1,2,4-triazolo[4,3-b]pyridazine This compound was prepared using the procedure described in Example 1 Step c) with (5-methylisoxazol-3-yl)methanol instead of (2-methyl-2H-1,2,4-triazol-3-yl)methanol. Data for the title compound: m.p.=150° C.; $^1$H NMR (360 MHz, CDCl$_3$) δ 1.92 (1H, m), 2.16 (3H, m), 2.40 (2H, m), 2.44 (3H, s), 3.63 (1H, m), 5.36 (2H, s), 6.01 (1H, s), 7.25–7.36 (2H, m), 7.55 (1H, m), 7.82 (1H, s), 7.89 (1H, m); MS (ES$^+$) m/c 380 [MH]$^+$. Anal. Found C, 62.99; H, 4.74; N, 18.09. C$_{20}$H$_{18}$FN$_5$O requires C, 63.32; H, 4.74; N, 18.46%.

EXAMPLE 16

7-Cyclobutyl-3-(2-fluorophenyl)-6-(1-methyl-1H-Imidazol-2-ylmethoxy)-1,2,4-triazolo[4,3-b]pyridazine This compound was prepared using the procedure described in Example 1 Step c) with (1-methyl-1H-imidazol-2-yl)methanol instead of (2-methyl-2H-1,2,4-triazol-3-yl)methanol. Data for the title compound: m.p.= 173° C.; $^1$H NMR (360 MHz, CDCl$_3$) δ 1.89 (1H, m), 2.10 (3H, m), 2.32 (2H, m), 3.61 (1H, m), 3.65 (3H, s), 5.40 (2H, s), 6.94 (1H, s), 7.06 (1H, s), 7.26–7.36 (2H, m), 7.55 (1H, m), 7.82 (1H, s), 7.92 (1H, m); MS (ES$^+$) m/e 379 [MH]$^+$.

EXAMPLE 17

7-Cyclobutyl-3-(2-fluorophenyl)-6-(4-methyl-4H-1,2,4-triazol-3-ylmethoxy)-1,2,4-triazolo[4,3-b]pyridazine This compound was prepared using the procedure described in Example 1 Step c) with (4-methyl-4H-1,2,4-triazol-3-yl)methanol instead of (2-methyl-2H-1,2,4-triazol-3-yl)methanol. Data for the title compound: m.p.=228° C.; $^1$H NMR (360 MHz, CDCl$_3$) δ 1.91 (1H, m), 2.10 (3H, m), 2.32 (2H, m), 3.56 (1H, m), 3.71 (3H, s), 5.54 (2H, s), 7.25–7.37 (2H, m), 7.56 (1H, m), 7.85 (1H, s), 7.89 (1H, m), 8.18 (1H, s); MS (ES$^+$) m/e 380 [MH]$^+$. Anal. Found C, 59.70; H, 4.74; N, 25.50. C$_{19}$H$_{11}$FN$_6$O requires C, 60.15; H, 4.78; N, 25.84%.

EXAMPLE 18

3-(2-Fluorophenyl)-6-(2-methyl-2H-1,2,4-triazol-3-ylmethoxy)-7-(thien-2-yl)-1,2,4-triazolo[4,3-b]pyridazine 0.9 Hydrate a) 4-Bromo-1,2-dihydropyridazine-3,6-dione Hydrazine hydrate (28 ml, 576 mmol) was added dropwise to a stirred solution of bromomaleic anhydride (100 g, 565 mmol) in THF (1 l) cooled in an ice-bath so that the internal temperature did not exceed 10° C. After complete addition of the hydrazine the mixture was refluxed for 18 h. Solvent was removed by evaporation and the residues were dried by azeotroping with toluene. The residue was triturated and washed with diethyl ether to give the title compound as an orange solid (83 g, 77%). $^1$H NMR (250 MHz, d$_6$-DMSO) δ 7.68 (1H, br s). MS (ES$^+$) m/e 193 [MH]$^+$, 191 [MH]$^+$. This material was used without further purification.

b) 3,6-Dichloro-4-(thien-2-yl)pyridazine

A mixture of 4-bromo-1,2-dihydropyridazine-3,6-dione (9 g, 47 mmol), 2-thiopheneboronic acid (7 g, 55 mmol), sodium carbonate (11.7 g, 110 mmol) and tetrakis(triphenylphosphine)palladium(0) (5 g) in DME (250 ml) and water (100 ml) was degassed, flushed with nitrogen and refluxed for 18 h. Solvents were removed by evaporation and the residues were azeotroped with toluene. The resulting solid was diluted with dichloromethane (20 ml) and phosphorus oxychloride (70 ml) and refluxed for 4 h. The reaction mixture was cooled, added slowly to ice-water, basified with aqueous sodium hydrogen carbonate and extracted with dichloromethane. The organic layer was dried (Na$_2$SO$_4$), filtered and concentrated. Dry flash column chromatography, eluting with 30% ethyl acetate-hexane, gave the title compound as an orange solid (1.18 g, 11%). $^1$H NMR (360 MHz, CDCl$_3$) δ 7.24 (1H, dd, J 5 and 4 Hz), 7.65–7.68 (2H, m), 7.80 (1H, dd, J 4 and 1 Hz). MS (ES$^+$) m/e 231 [MH]$^+$, 233 [MH]$^+$, 235 [MH]$^+$.

c) 6-Chloro-3-(2-fluorophenyl)-7-(thien-2-yl)-1,2,4-triazolo[4,3-b]pyridazine

A mixture of 3,6-dichloro-4-(thien-2-yl)pyridazine from above (0.5 g, 2.1 mmol), 2-fluorobenzhydrazide (0.66 g, 4.3 mmol) and triethylamine hydrochloride (0.59 g, 4.3 mmol) in p-xylene (10 ml) was stirred and heated at reflux under nitrogen for 30 hours. Upon cooling the volatiles were removed in vacuo. The residue was partly purified by chromatography on silica gel eluting with 50%→66%→100% ethyl acetate-hexane to give the title compound as a yellow solid (0.19 g, 26%). MS (ES$^+$) m/e 33 1 [MH]$^+$, 333 [MH]$^+$. This material was used without further purification.

d) 3-(2-Fluorophenyl)-6-(2-methyl-2H-1,2,4-triazol-3-ylmethoxy)-7-(thien-2-yl)-1,2,4-triazolo[4,3-b]pyridazine 0.9 Hydrate To a solution of (2-methyl-2H-1,2,4-triazol-3-yl)methanol (0.11 g, 1.0 mmol) (prepared using the conditions described in EP-A-421210) in DMF (5 ml) was added sodium hydride (0.04 g of a 60% dispersion in oil, 1 mol eq) and the reaction mixture was stirred at room temperature for 30 min. After this time 6-chloro-3-(2-fluorophenyl)-7-(thien-2-yl)-1,2,4-triazolo[4,3-b]pyridazine (0.19 g, 0.57 mmol) was added and the reaction mixture was stirred at room temperature for 18 h. The reaction mixture was diluted with water (70 ml) and the precipitate was collected. The solid was purified by boiling in ethyl acetate and collecting the title compound as a yellow solid (0.01 g, 12%). $^1$H NMR (250 MHz, d$_6$-DMSO) δ 3.83 (3H, s), 5.64 (2H, s), 7.24 (1H, dd, J 4 and 4 Hz), 7.44–7.55 (2H, m), 7.66–7.71 (1H, m), 7.82 (1H, d, J=5 Hz), 7.96–8.01 (3H, m), 8.23 (1H, s). MS (ES$^+$) m/e 408 [MH]$^+$. Anal. Found C, 53.81; H, 3.62; N, 23.42%. C$_{19}$H$_{14}$FN$_7$OS.0.9(H$_2$O) requires C, 53.87; H, 3.76; N, 23.14% m.p. 189–190° C.

EXAMPLE 19

3-(2,4-Difluorophenyl)-6-(2-methyl-2H-1,2,4-triazol-3-ylmethoxy)-7-(thien-2-yl)-1,2,4-triazolo[4,3-b]pyridazine This compound was prepared as for Example 18 Steps a), b), c) and d) except that 2,4-difluorobenzhydrazide was used instead of 2-fluorobenzhydrazide in Step c). The title compound was isolated as a yellow solid (0.01 g). $^1$H NMR (360 MHz, CDCl$_3$) δ 3.90 (3H, s), 5.61 (2H, s), 7.00–7.16 (3H, m), 7.50 (1H, d, J=5 Hz), 7.63 (1H, d, J=4 Hz), 7.90–7.98 (2H, m), 8.29 (1H, s). MS (ES$^+$) m/e 426 [MH]$^+$. m.p. 209–212° C.

EXAMPLE 20

6-(1H-Benzimidazol-2-ylmethoxy)-7-cyclobutyl-3-(2,4-difluorophenyl)-1,2,4-triazolo[4,3-b]pyridazine a) 7-Cyclobutyl-3-(2,4-difluorophenyl)-6-[1-(2-trimethylsilanyl-ethoxymethyl)-1H-benzimidazol-2-ylmethoxy]-1,2,4-triazolo[4,3-b]pyridazine This compound was prepared using the procedures described in Example 1 Steps a), b) and c), using 2,4-difluorobenzhydrazide instead of 2-fluorobenzhydrazide in Step b), and using [1-(2-trimethylsilanyl-ethoxymethyl)-1H-benzimidazol-2-yl]methanol (prepared as described in *J. Org. Chem.*, 1986, 1891) instead of (2-methyl-2H-1,2,4-triazol-3-yl)methanol in Step c). Data for the title compound: $^1$H NMR (250 MHz, CDCl$_3$) δ 7.94 (3H, m), 7.59 (1H, m), 7.45 (2H, m), 7.14 (2H, m), 5.74 (2H, s), 5.65 (2H, s), 3.71 (1H, m), 3.59 (2H, t), 1.90–2.46 (6H, m), 0.93 (2H, t), 0.00 (9H, m); MS (ES$^+$) m/e 563 [MH]$^+$.

b) 6-(1H-Benzimidazol-2-ylmethoxy)-7-cyclobutyl-3-(2,4-difluoro-phenyl)-1,2,4-triazolo[4,3-b]pyridazine A solution of 7-cyclobutyl-3-(2,4-difluorophenyl)-6-[1-(2-trimethylsilanylethoxymethyl)-1H-benzimidazol-2-ylmethoxy]-1,2,4-triazolo[4,3-b]pyridazine (187 mg, 0.333 mmol) in 5M hydrochloric acid (10 ml) and ethanol (4 ml) was heated at 80° C. overnight, then concentrated in vacuo to remove solvents. Saturated potassium carbonate solution was added, then the mixture was diluted with water, filtered and the residual solid washed with water then ether and then dried. The residue was purified by flash chromatography on silica gel using ethyl acetate as eluent to give the title compound (60 mg, 42%). Data for the title compound: $^1$H NMR (250 MHz, CDCl$_3$) δ 10.62 (1H, br s), 7.85 (2H, m), 7.56 (1H, d, J=1.6 Hz), 7.48 (1H, br s), 7.32 (2H, m), 7.00 (2H, m), 5.65 (2H, s), 3.54 (1H, m), 2.24 (2H, m), 2.01 (3H, m), 1.80 (1H, m); MS (ES$^+$) m/e 433 [MH]$^+$.

EXAMPLE 21

3-(2,4-Difluorophenyl)-6-(2-methyl-2H-1,2,4-triazol-3-ylmethoxy)-7-(pyrrolidin-1-yl)-1,2,4-triazolo[4,3-b]pyridazine a) 4-Bromo-3,6-dichloropyridazine A solution of 4-bromo-1,2-dihydropyridazine-3,6-dione (Example 18, Step a) (10 g, 52 mmol) in phosphorus-oxychloride (100 ml) was stirred and heated at 100° C. under nitrogen for 16 hours. Upon cooling the excess phosphorus oxychloride was removed it vacuo. The residue was azeotroped with toluene (×2), then taken up in dichloromethane/water. The mixture was carefully basified with sodium hydrogen carbonate (solid). It was necessary to dilute the mixture further to get two clear layers. The two layers were separated and the aqueous was extracted with dichloromethane (×3). The combined extracts were dried (Na$_2$SO$_4$), filtered and evaporated. The residue was purified by chromatography on silica gel, eluting with dichloromethane to afford the title pyridazine (5.0 g, 42%) as a colourless solid. $^1$H NMR (250 MHz, CDCl$_3$) 7.68 (br s). MS (ES$^+$) 230 [MH]$^+$, 228 [MH]$^+$.

b) 3,6-Dichloro-4-(pyrrolidin-1-yl)pyridazine

Pyrrolidine (3.36 ml, 40 mmol) was added to a stirred solution/suspension of 4-bromo-3,6-dichloropyridazine (8.3 g, 36 mmol) and potassium carbonate (13.8 g, 0.1 mol) in dry DMF (100 ml) at room temperature under nitrogen. The mixture was stirred at room temperature for 16 hours, then at 60° C. for 3 hours. The reaction was poured into water (250 ml). The aqueous was extracted with ethyl acetate (×3). The combined extracts were dried (MgSO$_4$), filtered and evaporated. The residue was purified by chromatography on silica gel, eluting with 0.5% methanol/dichloromethane to afford the title pyridazine (7.2 g, 92%) as a colourless oil. $^1$H NMR (250 MHz, CDCl$_3$) 2.00–2.05 (4H, m), 3.61–3.69 (4H, m), 6.46 (1H, s). MS (ES$^+$) 218 [MH]$^+$, 220 [MH]$^+$.

c) 3-Chloro-6-hydrazine-4-(pyrrolidin-1-yl)pyridazine 3,6-Dichloro-4-(pyrrolidin-1-yl)pyridazine (7.2 g, 33 mmol) and hydrazine hydrate (9.96 g, 0.2 mol) were heated at reflux in dioxan (130 ml) for 6 hours. Upon cooling the desired isomer crystallized from the reaction and was collected by filtration (4.1 g, 58%). $^1$H NMR (250 MHz, d$_6$-DMSO) 1.79–1.84 (4H, m), 3.25–3.40 (4H, m), 4.12 (2H, br), 6.09 (1H, s), 7.47 (1H, s). MS (ES$^+$) 214 [MH]$^+$, 216 [MH]$^+$.

d) N-[6-Chloro-5-(pyrrolidin-1-yl)-pyridazin-3-yl]-N'-(2,4-difluoro-benzylidene)hydrazine 3-Chloro-6-hydrazino-4-(pyrrolidin-1-yl)pyridazine (1.06 g, 4.9 mmol) and 2,4-difluorobenzaldehyde (437 ml, 4.9 mmol) were stirred in 0.2M hydrochloric acid (30 ml) for 2 hours. The precipitated imine was then collected by filtration and dried (1.37 g, 92%). MS (ES$^+$) 338 [MH]$^+$, 340 [MH]$^+$.

e) 6-Chloro-3-(2,4-difluorophenyl)-7-(pyrrolidin-1-yl)-1,2,4-triazolo[4,3-b]pyridazine Ferric chloride (4.74 g, 17.5 mmol) in ethanol (30 ml) was added dropwise to a solution of the foregoing imine (1.06 g, 3.5 mmol) in ethanol (60 ml) and heated at 60° C. After 6 hours the reaction mixture was partitioned between dichloromethane (250 ml) and brine (250 ml). The organic phase was dried (MgSO$_4$), filtered and evaporated. The residue was purified by chromatography on silica gel, eluting with ethyl acetate-hexane mixtures to afford the title pyridazine (0.7 g, 66%). $^1$H NMR (250 MHz, CDCl$_3$) 2.02–2.08 (4H, m), 3.53–3.58 (4H, m), 6.98–7.09 (2H, m), 7.46–7.56 (1H, m), 7.81–7.92 (1H, m). MS (ES$^+$) 336 [MH]$^+$, 338 [MH]$^+$.

f) 3-(2,4-Difluorophenyl)-6-(2-methyl-2H-1,2,4-triazol-3-ylmethoxy)-7-(pyrrolidin-1-yl)-1,2,4-triazolo[4,3-b]pyridazine Sodium hydride (60% dispersion in oil, 16 mg, 0.41 mmol) was added to a solution of (2-methyl-2H-1,2,4-triazol-3-yl)methanol (prepared using the conditions described in EP-A-421210) (38 mg, 0.33 mmol) in dry DMF (2 ml) at room temperature. After 1 h at room temperature a solution of 6-chloro-3-(2,4-difluorophenyl)-7-(pyrrolidin- 1-yl)-1,2,4-triazolo[4,3-b]pyridazine (102 mg, 0.30 mmol) was added and the reaction stirred for 18 hours. The residue was partitioned between dichloromethane and water. The aqueous was further extracted with dichloromethane (2×100 ml). The combined extracts were dried ($Na_2SO_4$), filtered and evaporated. The residue was purified by chromatography on silica gel, eluting with 0–2% ethyl acetate-methanol to afford the title pyridazine (42 mg, 30%). $^1$H NMR (250 MHz, $CDCl_3$) 1.73–1.78 (4H, m), 3.51–3.55 (4H, m), 3.93 (3H, s), 5.40 (2H, s), 6.65 (1H, s), 6.95–7.03 (2H, m), 7.92–7.94 (1H, m), 8.04 (1H, s), MS ($ES^+$) 413 $[MH]^+$.

EXAMPLE 22

3-(2,4-Difluorophenyl)-6-(1-methyl-1H-1,2,4-triazol-3-ylmethoxy)-7-(pyrrolidin-1-yl)-1,2,4-triazolo[4,3-b]pyridazine This compound was prepared as described in Example 21 Step f), using (1-methyl-1H-1,2,4-triazol-3-yl)methanol (EP-A-421210) instead of (2-methyl-2H-1,2,4-triazol-3-yl)methanol. Data for the title compound: $^1$H NMR (250 MHz, $CDCl_3$) 1.95–2.00 (4H, m), 3.46–3.52 (4H, m), 3.86 (3H, s), 5.47 (2H, s), 6.70 (1H, s), 6.95–7.11 (2H, m), 7.78–7.87 (1H, m), 7.90 (1H, s). MS ($ES^+$) 413 $[MH]^+$.

EXAMPLE 23

3-(2-Fluorophenyl)-6-(1-methyl-1H-1,2,4-triazol-3-ylmethoxy)-7-(pyrrolidin-1-yl)-1,2,4-triazolo[4,3-b]pyridazine Prepared in an analogous procedure as outlined in Example 21 Steps d), e) and f), using 2-fluorobenzaldehyde instead of 2,4-difluorobenzaldehyde in Step d) and (1-methyl-1H-1,2,4-triazol-3-yl)methanol (EP-A-421210) instead of (2-methyl-2H-1,2,4-triazol-3-yl)methanol in Step f), to afford the title pyridazine. $^1$H NMR (250 MHz, $d_6$-DMSO) 2.06–2.20 (4H, m), 3.68–3.74 (4H, m), 4.00 (3H, s), 5.72 (2H, s), 7.07 (1H, s), 7.60–7.70 (2H, m), 7.81–7.87 (1H, m), 8.05–8.11 (1H, m), 8.17 (1H, s). MS ($ES^+$) 395 $[MH]^+$.

EXAMPLE 24

7-Cyclobutyl-3-(2-fluorophenyl)-6-(1-methyl-1H-imidazol-4-ylmethoxy)-1,2,4triazolo[4,3-b]pyridazine This compound was prepared using the procedure described in Example 1 Step c) with (1-methyl-1H-imidazol-4-yl)methanol instead of (2-methyl-2H-1,2,4-triazol-3-yl)methanol. Data for the title compound: m.p.176° C.; $^1$H NMR (360 MHz, $CDCl_3$) δ 1.87 (1H, m), 2.10 (3H, m), 2.36 (2H, m), 3.59 (1H, m), 3.64 (3H, s), 5.28 (2H, s), 6.82 (1H, s), 7.26–7.36 (2H, m), 7.39 (1H, s), 7.53 (1H, m), 7.76 (1H, s), 7.92 (1H, m); MS ($ES^+$) m/e 379 $[MH]^+$.

EXAMPLE 25

7-(1-Fluorocyclobutyl)-3-(2-fluorophenyl)-6-(2-methyl-2H-1,2,4-triazol-3-ylmethoxy)-1,2,4-triazolo[4,3-b]pyridazine a) 3-Chloro-6-hydrazino-4-(trimethylsilyl)pyridazine To a solution of 3,6-dichloro-4-(trimethylsilyl)pyridazine (9.67 g, 43.7 mmol) (Turck et al., *J. Heterocycl. Chem.*, 1990, 27, 1377; prepared using the method described by Trécourt et al., *J. Heterocycl. Chem.*, 1995, 32, 1057) in a 1.0 M solution of hydrazine in THF (131 ml, 131 mmol) was added N,N-diisopropylethylamine (7.5 ml, 43.8 mmol) and the mixture was stirred at reflux under nitrogen for 68 h. The mixture was allowed to cool, silica gel was added and the solvent was evaporated in vacuo. The residue was then purified by flash chromatography (silica gel, 5% MeOH/$CH_2Cl_2$) to give 1.24 g (13%) of 6-chloro-3-hydrazino-4-(trimethylsilyl)pyridazine and 6.34 g (67%) of the title compound as a yellow-brown solid; $^1$H NMR (360 MHz, $CDCl_3$) δ 0.39 (9H, s), 3.96 (2H, br s), 6.24 (1H, br s), 7.08 (1H, s).

b) 3-Chloro-6-[2-(2-fluorobenzoyl)hydrazino]-4-(trimethylsilyl)-pyridazine

To a stirred mixture of 3-chloro-6-hydrazino-4-(trimethylsilyl)pyridazine (6.34 g, 29.3 mmol) and anhydrous triethylamine (4.9 ml, 35.2 mmol) in anhydrous diethyl ether (100 ml), cooled under nitrogen to −4° C., was added dropwise, over 13 min, 2-fluorobenzoyl chloride (3.5 ml, 29.4 mmol) keeping the temperature below 5° C. The thick mixture was then stirred for 30 min at 0–5° C., then quenched with anhydrous methanol (1 ml). The mixture was diluted with hexane (100 ml) and filtered. The collected solid was washed with diethyl ether (2×25 ml), then water (100 ml), then dissolved in dichloromethane (300 ml) and methanol (20 ml), washed with saturated aqueous NaCl (100 ml), dried ($Na_2SO_4$), and evaporated in vacuo to leave 9.72 g (98%) of the title compound as a pale brown solid; $^1$H NMR (360 MHz, $CDCl_3$) δ 0.36 (9H, s), 7.07 (1H, s), 7.20 (1H, dd, J=11.7 and 8.2 Hz), 7.30 (1H, t, J=7.6 Hz), 7.55 (1H, m), 8.00 (1H, br s), 8.07 (1H, td, J=7.7 and 1.8 Hz), 9.19 (1H, br s); MS ($ES^+$) m/e 339/341 $[MH]^+$, 217/219 $[M-COC_6H_4F+2H]^+$.

c) 6-Chloro-3-(2-fluorophenyl)-7-(trimethylsilyl)-2,4-triazolo[4,3-b]pyridazine

To a stirred suspension of 3-chloro-6-[2-(2-fluorobenzoyl)hydrazino]-4-(trimethylsilyl)pyridazine (9.72 g, 28.7 mmol) and 1,2-dibromotetrachloroethane (18.68 g, 57.4 mmol) in anhydrous acetonitrile (170 ml), cooled under nitrogen to 1° C., was added portionwise, over 21 min, solid triphenylphosphine (30.10 g, 115 mmol), keeping the temperature below 5° C. The mixture was stirred at 2° C. for 10 min, then anhydrous triethylamine (32.0 ml, 230 mmol) was added dropwise over 18 min, keeping the temperature below 6° C. The mixture was then stirred at 0–3° C. under nitrogen for 85 min. The mixture was then diluted with dichloromethane (150 ml) and washed with water (200 ml). The organic: layer was dried ($Na_2SO_4$) and evaporated in vacuo. The residue was purified by flash chromatography (silica gel, 20–40% EtOAc/hexane) to afford 7.67 g (83%) of the title compound as a white solid; $^1$H NMR (360 MHz, $CDCl_3$) δ 0.48 (9H, s), 7.30 (1H, dd, J=10.1 and 8.8 Hz), 7.36 (1H, td, J=7.6 and 1.1 Hz), 7.58 (1H, m), 7.90 (1H, td, J=7.3 and 1.8 Hz), 8.30 (1H, s); MS ($ES^+$) m/e 321/323 $[MH]^+$.

d) 6-Chloro-3-(2-fluorophenyl)-7-(1-hydroxycyclobutyl)-1,2,4-triazolo[4,3-b]pyridazine To a stirred solution of 6-chloro-3-(2-fluorophenyl)-7-(trimethylsilyl)-1,2,4-triazolo[4,3-b]pyridazine (1.04 g, 3.24 mmol) in anhydrous THF (15 ml) under nitrogen was added cyclobutanone (1.21 ml, 16.2 mmol), followed by solid tetrabutylammonium difluorotriphenylstannate (0.410 g, 0.650 mmol). The flask was evaporated and refilled with nitrogen four times, then stirred at room temperature for 5.75 h. More tetrabutylammonium difluorotriphenylstannate (0.403 g, 0.639 mmol) was added and the mixture was stirred for a further 36 h. The mixture was then partitioned between dichloromethane (75 ml) and water (75 ml). The aqueous layer was extracted further with dichloromethane (2×50 ml), and the combined organic extracts were dried (Na$_2$SO$_4$) and evaporated ill vacuo. The residue was purified by flash chromatography (silica gel, 70–100% EtOAc/hexane) to give 0.2634 g (26%) of the title compound as a cream solid; $^1$H NMR (360 MHz, CDCl$_3$) δ 1.81 (1H, m), 2.27 (1H, m), 2.52 (2H, m), 2.72 (2H, m), 2.87 (1H, s), 7.30 (1H, t, J=9.3 Hz), 7.36 (1H, t, J=7.5 Hz), 7.58 (1H, m), 7.88 (1H, td, J=7.3 and 1.8 Hz), 8.12 (1H, s); MS (ES$^+$) m/e 319/321 [MH]$^+$, 249.

e) 7-(1-Fluorocyclobutyl)-3-(2-fluorophenyl)-6-(2-methyl-2H-1,2,4-triazol-3-ylmethoxy)-1,2,4-triazolo[4,3-b]pyridazine To a stirred solution of (2-methyl-2H-1,2,4-triazol-3-yl)methanol (0.2206 g, 1.95 mmol) in anhydrous DMF (6 ml) under nitrogen was added sodium hydride (60% dispersion in oil, 77.7 mg, 1.94 mmol) and the mixture was stirred at room temperature for 20 min. The mixture was then cooled in an ice-water bath and a solution of 6-chloro-3-(2-fluorophenyl)-7-(1-hydroxycyclobutyl)-1,2,4-triazolo[4,3-b]pyridazine (0.2573 g, 0.807 mmol) in anhydrous DMF (5 ml) was added dropwise over 5 min. The mixture was stirred for 20 min under nitrogen, then poured into saturated aqueous NH$_4$Cl (50 ml), saturated aqueous NaCl (25 ml), and dichloromethane (75 ml). The aqueous-layer was further extracted with dichloromethane (2×50 ml), and the combined organic extracts were dried (Na$_2$SO$_4$) and evaporated in vacuo. The residue was purified by flash chromatography (silica gel, 3–5% MeOH/CH$_2$Cl$_2$) to afford 0.2793 g of 3-(2-fluorophenyl)-7-(1-hydroxycyclobutyl)-6-(2-methyl-2H-1,2,4-triazol-3-ylmethoxy)-1,2,4-triazolo[4,3-b]pyridazine (containing approximately 20% of (2-methyl-2H-1,2,4-triazol-3-yl)methanol starting material) as a colourless solid; $^1$H NMR (360 MHz, CDCl$_3$) δ 1.74 (1H, m), 2.17 (1H, m), 2.43 (2H, m), 2.60 (2H, m), 3.82 (3H, s), 5.58 (2H, s), 7.27 (1H, t, J=9.6 Hz), 7.36 (1H, t, J=7.5 Hz), 7.58 (1H, m), 7.82 (1H, m), 7.85 (1H, s), 8.01 (1H, s); MS (ES$^+$) m/e 396 [MH]$^+$, 114.

To a stirred solution of the above material (0.2094 g) in anhydrous dichloromethane (10 ml), cooled to −78° C. under nitrogen, was added diethylaminosulfur trifluoride (DAST) (77.0 ml, 0.582 mmol) dropwise and the mixture was stirred at <−70° C. More DAST (2×77.0 ml, 0.582 mmol and 40 ml, 0.303 mmol) was added dropwise after 40, 70 and 110 min, respectively. The mixture was stirred at <−70° C. for a further 40 min, then partitioned between saturated aqueous NaHCO$_3$ (20 ml) and dichloromethane (40 ml). The aqueous layer was extracted with more dichloromethane (2×30 ml), and the combined organic extracts were dried (Na$_2$SO$_4$) and evaporated in vacuo. The residue was purified by flash chromatography (silica gel, 2% MeOH/CH$_2$Cl$_2$) to give 0.1249 g (52%) of the title compound as a white solid; m.p. 154–162° C. (CH$_2$Cl$_2$-EtOAc-hexane), $^1$H NMR (400 MHz, DMSO-d$_6$) δ 1.60 (1H, m), 1.96 (1H, m), 2.51 (2H, m), 2.86 (2H, m), 3.78 (3H, s), 5.55 (2H, s), 7.46 (1H, t, J=7.8 Hz), 7.50 (1H, t, J=9.8 Hz), 7.70 (1H, m), 7.93 (1H, m), 7.94 (1H, s), 8.59 (1H, d, J=3.0 Hz); MS (ES$^+$) m/e 398 [MH]$^+$, 378 [M−HF+H]$^+$. Anal. Found C, 57.61; H, 4.18; N, 24.47%. C$_{19}$H$_{17}$F$_2$N$_7$O requires C, 57.43; H, 4.31; N, 24.67%.

EXAMPLE 26

7-Cyclobutyl-3-(2-fluorophenyl)-6-(2-methyl-2H-pyrazol-3-ylmethoxy)-1,2,4-triazolo[4,3-b]pyridazine This compound was prepared using the procedure described in Example 1 Step c) with (2-methyl-2H-pyrazol-3-yl)methanol (prepared using the conditions described in EP-A-91130) used instead of (2-methyl-2H-1,2,4-triazol-3-yl)methanol. Data for the title compound: m.p. 184–186° C.; $^1$H NMR (360 MHz, DMSO) δ 1.80 (1H, m), 1.99 (1H, m), 2.21 (4H, m), 3.57 (1H, m), 3.80 (3H, s), 5.39 (2H, s), 6.29 (1H, s), 7.37 (1H, s), 7.48 (2H, m), 7.64 (1H, m), 7.96 (1H, m), 8.18 (1H, s); MS (ES$^+$) m/e 379 [MH]$^+$.

EXAMPLE 27

7-(2,2-Dimethylpropyl)-3-(2-fluorophenyl)-6-(2-methyl-2H-1,2,4-triazol-3-ylmethoxy)-1,2,4-triazolo[4,3-b]pyridazine a) 7-Bromo-6-chloro-3-(2-fluorophenyl)-1,2,4-triazolo[4,3-b]pyridazine Tetrabutylammonium difluorotriphenylstannate (6.8 g, 10.8 mmol) was added to a suspension of 6-chloro-3-(2-fluorophenyl)-7-(trimethylsilyl)-1,2,4-triazolo[4,3-b]pyridazine (3.17 g, 9.88 mmol), prepared as in Example 25 Step c), and 1,2-dibromotetrafluoroethane (6.0 ml, 50 mmol) in anhydrous THF (75 ml) and-the mixture was stirred at room temperature under nitrogen for 18 h. The mixture was diluted with dichloromethane (100 ml), filtered and the filtrate was concentrated. Flash column chromatography on silica gel, eluting with 50–100% EtOAc-hexane, gave 7-bromo-6-chloro-3-(2-fluorophenyl)-1,2,4-triazolo[4,3-b]pyridazine (2.84 g, 88%) as an off-white solid; $^1$H NMR (360 MHz, CDCl$_3$) δ 7.31 (1H, dd, J=10 and 10 Hz), 7.36 (1H, ddd, J=8, 8 and 1 Hz), 7.57–7.63 (1H, m), 7.87 (1H, ddd, J=7, 7 and 2 Hz), 8.49 (1H, s); MS (ES$^+$) m/e 327/329/331 [MH]$^+$.

b) 7-Bromo-3-(2-fluorophenyl)-6-(2-methyl-2H-1,2,4-triazol-3-ylmethoxy)-1,2,4-triazolo[4,3-b]pyridazine A solution of potassium bis(trimethylsilyl)amide in toluene (16.8 ml, 0.5M, 8.4 mmol) was added to a stirred solution of (2-methyl-2H-1,2,4-triazol-3-yl)methanol (0.95 g, 8.4 mmol) in anhydrous THF (30 ml) at room temperature under nitrogen. After 20 min the suspension was cooled to 0° C. and a suspension of 7-bromo-6-chloro-3-(2-fluorophenyl)-1,2,4-triazolo[4,3-b]pyridazine (2.28 g, 6.96 mmol) in anhydrous THF (100 ml) was added dropwise. The mixture was stirred for 3 h at 0° C. then poured into ice-water (400 ml), diluted with saturated aqueous ammonium chloride (100 ml) and extracted with dichloromethane-methanol (9:1, 3×100 ml). The extracts were dried (Na$_2$SO$_4$), filtered and concentrated. Flash column chromatography on silica gel, eluting with 3% methanol-dichloromethane, gave 7-bromo-3-(2-fluorophenyl)-6-(2-methyl-2H-1,2,4-triazol-3-ylmethoxy)-1,2,4-triazolo[4,3-b]pyridazine (1.45 g, 52%) as a yellow solid; $^1$H NMR (360 MHz, CDCl$_3$) δ 3.95 (3H, s), 5.54 (2H, s), 7.28 (1H, dd, J=10 and 10 Hz), 7.37 (1H, ddd, J=8, 8 and 1 Hz), 7.57–7.63 (1H, m), 7.86 (1H, ddd, J=8, 8 and 2 Hz), 7.90 (1H, s), 8.41 (1H, s); MS (ES$^+$) m/e 404/406 [MH]$^+$.

c) 7-(2,2-Dimethylpropyl)-3-(2-fluorophenyl)-6-(2-methyl-2H-1,2,4-triazol-3-ylmethoxy)-1,2,4-triazolo[4,3-b]pyridazine 1,2-Dibromoethane (0.03 ml, 10 mol %) was added to a stirred suspension of acid washed zinc dust (0.45 g, 7.0 mmol) in anhydrous DMF (3 ml) at 50° C. under nitrogen. After 5 min, neopentyl iodide (1.0 ml, 7.5 mmol) was added. The mixture was stirred for 2.5 h to give a grey-green milky solution. A mixture of 7-bromo-3-(2-fluorophenyl)-6-(2-methyl-2H-1,2,4-triazol-3-ylmethoxy)-1,2,4-triazolo[4,3-b]pyridazine (0.35 g, 0.866 mmol), tri-2-furylphosphine (0.08 g, 40 mol %) and tris(dibenzylideneacetone)dipalladium(0) (0.04 g, 5 mol %) in anhydrous DMF (2 ml) was stirred at 50° C. under nitrogen for 15 min followed by addition of the solution of organozinc reagent via syringe. After 2.5 h, the mixture was cooled, poured into water (100 ml) and extracted with dichloromethane (2×50 ml). The extracts were dried ($Na_2SO_4$), filtered and concentrated. Flash column chromatography on silica gel, eluting with 2% methanol-dichloromethane, gave a brown solid that was recrystallised from ethyl acetate-diethyl ether to give 7-(2,2-dimethylpropyl)-3-(2-fluorophenyl)-6-(2-methyl-2H-1,2,4-triazol-3-ylmethoxy)-1,2,4-triazolo[4,3-b]pyridazine (0.199 g, 58%) as a beige powder; $^1$H NMR (360 MHz, $CDCl_3$) δ 0.96 (9H, s), 2.61 (2H, s), 3.83 (3H, s), 5.47 (2H, s), 7.28 (1H, dd, J=10 and 10 Hz), 7.36 (1H, dd, J=8 and 8 Hz), 7.56–7.62 (1H, m), 7.83 (1H, s), 7.86 (1H, dd, J=8 and 8 Hz), 7.90 (1H, s); MS (ES$^+$) m/e 396 [MH]$^+$. Anal. Found C, 59.66; H, 5.69; N, 24.41%. $C_{20}H_{22}FN_7O.0.4H_2O$ requires C, 59.66; H, 5.71; N, 24.35%.

EXAMPLE 28

3-(2-Fluorophenyl)-7-(2-methylpropyl)-6-(2-methyl-2H-1,2,4-triazol-3-ylmethoxy)-1,2,4-triazolo[4,3-b]pyridazine This compound was prepared using the procedure described in Example 27 Step c) with 1-iodo-2-methylpropane used instead of neopentyl iodide. Data for the title compound: m.p. 134–136° C. (EtOAc); $^1$H NMR (360 MHz, $CDCl_3$) δ 0.97 (6H, d, J=7 Hz), 1.92–2.60 (1H, m), 2.54 (2H, d, J=7 Hz), 3.84 (3H, s), 5.49 (2H, s), 7.25–7.30 (1H, m), 7.36 (1H, dd, J=8 and 8 Hz), 7.56–7.62 (1H, m), 7.83 (1H, s), 7.83–7.87 (1H, m), 7.89 (1H, s); MS (ES$^+$) m/e 382 [MH]$^+$. Anal. Found C, 59.66; H, 5.39; N, 25.56%. $C_{19}H_{20}FN_7O$ requires C, 59.83; H, 5.29; N, 24.71%.

EXAMPLE 29

3-(2-Fluorophenyl)-7-(3-methylbutyl)-6-(2-methyl-2H-1,2,4-triazol-3-ylmethoxy)-1,2,4-triazolo[4,3-b]pyridazine This compound was prepared using the procedure described in Example 27 Step c) with 1-iodo-3-methylbutane used instead of neopentyl iodide. Data for the title compound: m.p. 103–105° C. (EtOAc); $^1$H NMR (360 MHz, $CDCl_3$) δ 0.95 (6H, d, J=6 Hz), 1.15–1.57 (2H, m), 1.61–1.70 (1H, m), 2.66 (2H, dd, J=8 and 8 Hz), 3.85 (3H, s), 5.50 (2H, s), 7.24–7.30 (1H, m), 7.35 (1H, dd, J=7 and 7 Hz), 7.52–7.60 (1H, m), 7.82–7.86 (1H, m), 7.85 (1H, s), 7.89 (1H, s); MS (ES$^+$) m/e 396 [MH]$^+$. Anal. Found C, 60.56; H, 5.61%. $C_{20}H_{22}FN_7O$ requires C, 60.75; H, 5.61%.

EXAMPLE 30

7-Cyclopentylmethyl-3-(2-fluorophenyl)-6-(2-methyl-2H-1,2,4-triazol-3-ylmethoxy)-1,2,4-triazolo[4,3-b]pyridazine a) 3-(2-Fluorophenyl)-7-iodo-6-(2-methyl-2H-1,2,4-triazol-3-ylmethoxy)-1,2,4-triazolo[4,3-b]pyridazine A solution of 6-chloro-3-(2-fluorophenyl)-7-(trimethylsilyl)-1,2,4-triazolo[4,3-b]pyridazine (5.0 g, 15.6 mmol), prepared as in Example 25 Step c), and 1,2-diiodoethane (14 g, 50 mmol) in anhydrous THF (150 ml) was added via cannula to a stirred suspension of tris(dimethylamino)-sulfur (trimethylsilyl)difluoride (5.0 g, 18 mmol) in anhydrous THF (200 ml) at room temperature under nitrogen. After 18 h, the mixture was diluted with dichloromethane (400 ml) and washed sequentially with water (300 ml) and brine (200 ml). The organic layer was dried ($Na_2SO_4$), filtered and concentrated. Flash column chromatography on silica gel, eluting with 3% methanol-dichloromethane, gave crude 6-chloro-3-(2-fluorophenyl)-7-iodo-1,2,4-triazolo[4,3-b]pyridazine (3.54 g) as a dark brown solid. This was subjected to the conditions described in Example 27 Step b) to give 3-(2-fluorophenyl)-7-iodo-6-(2-methyl-2H-1,2,4-triazol-3-ylmethoxy)-1,2,4-triazolo[4,3-b]pyridazine (1.32 g, 19% over two steps) as a yellow solid; $^1$H NMR (360 MHz, $CDCl_3$) δ 3.97 (3H, s), 5.51 (2H, s), 7.28 (1H, dd, J=8 and 8 Hz), 7.37 (1H, dd, J=8 and 8 Hz), 7.56–7.64 (1H, m), 7.86 (1H, ddd, J=7, 7 and 1 Hz), 7.90 (1H, s), 8.68 (1H, s); MS (ES$^+$) m/e 452 [MH]$^+$.

b) 7-Cyclopentylmethyl-3-(2-fluorophenyl)-6-(2-methyl-2H-1,2,4-triazol-3-ylmethoxy)-1,2,4-triazolo[4,3-b]pyridazine This compound was prepared using the procedure described in Example 27 Step c) with cyclopentylmethyl iodide used instead of neopentyl iodide and 3-(2-fluorophenyl)-7-iodo-6-(2-methyl-2H-1,2,4-triazol-3-ylmethoxy)-1,2,4-triazolo[4,3-b]pyridazine used instead of 7-bromo-3-(2-fluorophenyl)-6-(2-methyl-2H-1,2,4-triazol-3-ylmethoxy)-1,2,4-triazolo[4,3-b]pyridazine. Data for the title compound: m.p. 135–137° C.; $^1$H NMR (360 MHz, $CDCl_3$) δ 1.18–1.28 (2H, m), 1.36–1.74 (4H, m), 1.76–1.86 (2H, m), 2.16–2.28 (1H, m), 2.66 (2H, d, J=7 Hz), 3.84 (3H, s), 5.49 (2H, s), 7.25–7.30 (1H, m), 7.36 (1H, dd, J=7 and 7 Hz), 7.50–7.60 (1H, m), 7.82–7.86 (2H, m), 7.89 (1H, s); MS (ES$^+$) m/e 382 [MH]$^+$. Anal. Found C, 60.85; H, 5.38%. $C_{21}H_{22}FN_7O.0.4H_2O$ requires C, 60.83; H, 5.54%.

EXAMPLE 31

7-(3-Benzyloxycyclobutyl)-3-(2-fluorophenyl)-6-(2-methyl-2H-1,2,4-triazol-3-ylmethoxy)-1,2,4-triazolo[4,3-b]pyridazine a) cis-3-benzyloxy-1-hydroxycyclobutane A mixture of 3-benzyloxycyclobutan-1-one (0.92 g, 5.22 mmol) (Ogura et al., *Bull. Chem. Soc. Jpn.*, 1984, 57, 1637–1642) and sodium borohydride (0.20 g, 5.29 mmol) in ethanol (15 ml) was stirred at room temperature for 3.5 h. The mixture was filtered, washing with ethanol, and the filtrate was concentrated. Filtration through a plug of silica, eluting with ethyl acetate, gave cis-3-benzyloxy-1-hydroxycyclobutane (0.854 g, 92%) as a colourless oil; $^1$H NMR (250 MHz, $CDCl_3$) δ1.75–2.00 (2H, m), 2.65–2.79 (2H, m), 3.62 (1H, qn, J=7 Hz), 3.90 (1H, broad qn, J=7 Hz), 4.41 (2H, s), 7.23–7.47 (5H, m).

b) cis-3-benzyloxy-1-methanesulfonyloxycyclobutane

Methanesulfonyl chloride (0.44 ml, 5.7 mmol) was added dropwise to a stirred solution of cis-3-benzyloxy-1-hydroxycyclobutane (0.85 g, 4.77 mmol) and triethylamine (1.0 ml, 7.2 mmol) in dry dichloromethane (15 ml) at 0° C. under nitrogen. The white suspension was stirred at 0° C. for 1.5 h then poured into water (50 ml) and extracted with dichloromethane (2×30 ml). The extracts were dried ($Na_2SO_4$), filtered and concentrated. The oil was filtered through a plug of silica gel, eluting with ethyl acetate, to give cis-3-benzyloxy-1-methanesulfonyloxycyclobutane (1.27 g, 100%) as a yellow oil; $^1$H NMR (250 MHz, $CDCl_3$) δ 2.26–2.39 (2H, m), 2.77–2.91 (2H, m), 2.97 (3H, s), 3.74 (1H, qn, J=7 Hz), 4.42 (2H, s), 4.68 (1H, qn, J=7 Hz), 7.26–7.42 (5H, m).

c) trans-3-benzyloxy-1-iodocyclobutane

A solution of cis-3-benzyloxy-1-methanesulfonyloxycyclobutane (1.25 g, 4.8 mmol) and sodium iodide (2.16 g, 14.4 mmol) in dry acetone (20 ml) was refluxed under nitrogen for 3.5 days. The mixture was cooled and diluted with diethyl ether (150 ml). The suspension was filtered and the filtrate was concentrated. The residue was dissolved in ethyl acetate and filtered through a plug of silica gel, eluting with ethyl acetate to give trans-3-benzyloxy-1-iodocyclobutane (1.19 g, 86%) as an orange oil; $^1$H NMR (250 MHz, CDCl$_3$) δ 2.54–2.65 (2H, m), 2.94–3.04 (2H, m), 3.85–4.06 (2H, m), 4.40 (2H, s), 7.26–7.38 (5H, m).

d) 7-(3-Benzyloxycyclobutyl)-3-(2-fluorophenyl)-6-(2-methyl-2H-1,2,4-triazol-3-ylmethoxy)-1,2,4-triazolo[4,3-b] pyridazine This compound was prepared using the procedure described in Example 27 Step c) with trans-3-benzyloxy-1-iodocyclobutane used instead of neopentyl iodide. The compound was isolated by preparative thin layer chromatography, eluting with 5% methanol-dichloromethane, then a second preparative thin layer chromatography, eluting with 2% ethanol-ethyl acetate, and trituration with diethyl ether to give a 2.3:1 mixture of trans:cis isomers; $^1$H NMR (360 MHz, CDCl$_3$) δ 2.00–2.10 and 2.18–2.26 (2H, m), 2.28–2.38 and 2.34–2.42 (2H, m), 3.00–3.10 and 3.68–3.78 (1H, m), 3.80 and 3.81 (3H, s), 4.02–4.22 (1H, m), 4.46 and 4.47 (2H, s), 5.46 and 5.47 (2H, s), 7.24–7.37 (7H, m), 7.56–7.60 (1H, m), 7.80–7.91 (3H, m); MS (ES$^+$) m/e 486 [MH]$^+$.

EXAMPLE 32

3-(2-Fluorophenyl)-7-(3-hydroxycyclobutyl)-6-(2-methyl-2H-1,2,4-triazol-3-ylmethoxy)-1,2,4-triazolo[4,3-b]pyridazine A mixture of 7-(3-benzyloxycyclobutyl)-3-(2-fluorophenyl)-6-(2-methyl-2H-1,2,4-triazol-3-ylmethoxy)-1,2,4-triazolo[4,3-b]pyridazine (0.04 g, 0.082 mmol), excess ammonium formate (1.0 g), formic acid (1 ml) and 10% palladium on carbon (0.10 g) was stirred at 60° C. under nitrogen for 18 h, then cooled and concentrated. The residue was diluted with dichloromethane (20 ml) and washed with brine (20 ml). The organic layer was dried (Na$_2$SO$_4$), filtered and concentrated. Preparative thin layer chromatogaphy on silica gel, eluting with 10% methanol-dichloromethane, gave recovered 7-(3-benzyloxycyclobutyl)-3-(2-fluorophenyl)-6-(2-methyl-2H-1,2,4-triazol-3-ylmethoxy)-1,2,4-triazolo[4,3-b]pyridazine (0.016 g, 40%) and 3-(2-fluorophenyl)-7-(3-hydroxycyclobutyl)-6-(2-methyl-2H-1,2,4-triazol-3-ylmethoxy)-1,2,4-triazolo[4,3-b]pyridazine (0.009 g, 28%) as a white solid, a 3:1 mixture of trans:cis isomers; $^1$H NMR (360 MHz, CDCl$_3$) δ 2.08–2.18, 2.36–2.56 and 2.70–2.84 (4H, m), 3.00–3.08 and 3.70–3.78 (1H, m), 3.82 (3H, s), 4.36–4.40 and 4.44–4.58 (1H, m), 5.47 (2H, s), 7.24–7.32 (1H, m), 7.43–7.40 (1H, m), 7.54–7.60 (1H, m), 7.82–7.96 (3H, m); MS (ES$^+$) m/e 396 [MH]$^+$.

EXAMPLES 33 & 34

7-(1-Fluorobut-3-enyl)-3-(2-fluorophenyl)-6-(2-methyl-2H-1,2,4-triazol-3-ylmethoxy)-1,2,4-triazolo[4,3-b]pyridazine and 7-(3-fluorocyclobutyl)-3-(2-fluorophenyl)-6-(2-methyl-2H-1,2,4-triazol-3-ylmethoxy)-1,2,4-triazolo[4,3-b]pyridazine Diethylaminosulfur trifluoride (0.025 ml, 0.17 mmol) was added dropwise at −78° C. to a stirred solution of 3-(2-fluorophenyl)-7-(3-hydroxycyclobutyl)-6-(2-methyl-2H-1,2,4-triazol-3-ylmethoxy)-1,2,4-triazolo[4,3-b]pyridazine (0.033 g, 0.083 mmol) in dry dichloromethane (3 ml) under nitrogen. After 3.5 h at −78° C., further diethylaminosulfur trifluoride (0.025 ml, 0.17 mmol) was added. The mixture was stirred at −78° C. for a further 1.25 h then warmed to 0° C. over 10 min and quenched by the addition of methanol (2 ml). The mixture was diluted with water (20 ml) and extracted with dichloromethane (2×20 ml). The extracts were dried (Na$_2$SO$_4$), filtered and concentrated. Preparative thin layer chromatography on silica gel, eluting with 5% methanol-dichloromethane, gave two products. The less polar material was 7-(1-fluorobut-3-enyl)-3-(2-fluorophenyl)-6-(2-methyl-2H-1,2,4-triazol-3-ylmethoxy)-1,2,4-triazolo [4,3-b]pyridazine (0.0023 g, 7%); $^1$H NMR (400 MHz, CDCl$_3$) δ 2.59–2.87 (2H, m), 3.85 (3H, s), 5.13 (1H, d, J=18 Hz), 5.16 (1H, d, J=10 Hz), 5.30 (2H, s), 5.49 (1H, d, J=13 Hz), 5.54 (1H, d, J=13 Hz), 5.64–5.85 (2H, m), 7.29 (1H, ddd, J=8, 8 and 1 Hz), 7.35–7.40 (1H, m), 7.55–7.62 (1H, m), 7.84 (1H, dd, J=8 and 8 Hz), 7.80 (1H, s), 8.15 (1H, s); MS (ES$^+$) m/e 398 [MH]$^+$. The more polar material was 7-(3-fluorocyclobutyl)-3-(2-fluorophenyl)-6-(2-methyl-2H-1,2,4-triazol-3-ylmethoxy)-1,2,4-triazolo[4,3-b]pyridazine (0.0014 g, 4%) as a 1:1 mixture of trans:cis isomers; $^1$H NMR (400 MHz, CDCl$_3$) δ 2.25–3.10 (4H, m), 3.81 and 3.82 (3H, s), 4.13–4.75 (1H, m), 4.96–5.27 (1H, m), 5.48 and 5.49 (2H, s), 7.26–7.30 (1H, m), 7.36 (1H, ddd, J=8, 8 and 1 Hz), 7.55–7.60 (1H, m), 7.79–7.91 (3H, m); MS (ES$^+$) m/e 398 [MH]$^+$.

EXAMPLE 35

3-(2-Fluorophenyl)-6-(2-methyl-2H-1,2,4-triazol-3-ylmethoxy)-7-trifluoromethyl-1,2,4-triazolo[4,3-b]pyridazine Iodotrifluoromethane (2.0 g, 10 mmol) was bubbled through a solution of 7-bromo-3-(2-fluorophenyl)-6-(2-methyl-2H-1,2,4-triazol-3-ylmethoxy)-1,2,4-triazolo[4,3-b]pyridazine (0.10 g, 0.25 mmol) in dry DMF (2 ml) at room temperature until the required quantity of gas had dissolved. Copper powder (0.16 g, 2.5 mmol) was added and the mixture was stirred in a sealed tube at 80° C. for 18 h. The mixture was cooled, diluted with dichloromethane (50 ml) and filtered. The filtrate was washed with water (50 ml), then dried (Na$_2$SO$_4$), filtered and concentrated. Preparative thin layer chromatography, eluting with 3% methanol-dichloromethane, gave 3-(2-fluorophenyl)-6-(2-methyl-2H-1,2,4-triazol-3-ylmethoxy)-7-trifluoromethyl-1,2,4-triazolo [4,3-b]pyridazine (0.0061 g, 6%) as a pale yellow solid; m.p. 123–126° C.; $^1$H NMR (360 MHz, CDCl$_3$) δ 3.92 (3H, s), 5.60 (2H, s), 7.31 (1H, dd, J=8 and 8 Hz), 7.40 (1H, dd, J=8 and 8 Hz), 7.56–7.64 (1H, m), 7.86–7.94 (2H, m), 8.50 (1H, s); MS (ES$^+$) m/e 393 [MH]$^+$.

EXAMPLE 36

3-(2-Fluorophenyl)-7-(4-methyltetrahydropyran-4-yl)-6-(2-methyl-2H-1,2,4-triazol-3-ylmethoxy)-1,2,4-triazolo [4,3-b]pyridazine a) 4-Methyltetrahydropyran-4-carboxylic Acid $^n$Butyllithium (21.1 ml, 33.8 mmol, 1.6 M in hexanes) was added dropwise over 10 minutes to a stirred solution of duisopropylamine (4.7 ml, 33.8 mmol) in anhydrous tetrahydrofuran (40 ml) under an atmosphere of nitrogen at <10° C. Upon addition, tetrahydropyran-4-carboxylic acid (*J. Am. Chem. Soc.*, 1993, 115, 8407) was added in anhydrous tetrahydrofuran (20 ml) under nitrogen at <5° C. The mixture was stirred at room temperature for one hour after which methyl iodide (2.4 ml, 38.4 mmol) was added dropwise at <5° C. The resultant solution was stirred at <5° C. for 30 minutes, allowed to warm to room temperature and stirred for a further 3.5 days. The solvent was removed by evaporation and the residue dissolved in dichloromethane (100 ml) and 2N hydrochloric acid (100 ml) added. The aqueous layer was extracted with dichloromethane (3×100 ml) and the combined organic layers were washed with water (100 ml), brine (100 ml), dried (MgSO$_4$), filtered and evaporated to yield the title product (1.4 g) which was used in the next step without purification. Data for the title compound: $^1$H NMR (250 MHz, CDCl$_3$) δ 1.00 (3H, s), 1.47–1.58 (2H, m), 2.06–2.11 (2H, m), 3.49–3.60 (2H, m), 3.78–3.86 (2H, m).

b) 3-(2-Fluorophenyl)-7-(4-methyltetrahydropyran-4-yl)-6-(2-methyl-2H-1,2,4-triazol-3-ylmethoxy)-1,2,4-triazolo[4,3-b]pyridazine This compound was prepared using the procedure described in Example 1, Steps a), b) and c) using 4-methyltetrahydropyran-4-carboxylic acid instead of cyclobutane carboxylic acid in Step a). Data for the title compound: m.p.=191° C.; $^1$H NMR (360 MHz, CDCl$_3$) δ 1.46 (3H, s), 1.89–1.94 (2H, m), 2.07–2.15 (2H, m), 3.73–3.79 (7H, m), 5.51 (2H, s), 7.28–7.30 (1H, m), 7.36 (1H, t, J=7.6 Hz), 7.57 (1H, m), 7.84 (1H, m), 7.88 (1H, s), 7.95 (1H, s); MS (ES$^+$) m/e 424 [MH]$^+$; Anal. Found: C, 59.40; H, 5.11; N, 23.13%. C$_{21}$H$_{22}$FN$_7$O$_2$ requires: C, 59.57; H, 5.24; N, 23.15%.

EXAMPLE 37

3-(2-Fluorophenyl)-7-(4-methyltetrahydropyran-4-yl)-6-(1-methyl-1H-1,2,4-triazol-3-ylmethoxy)-1,2,4-triazolo [4,3-b]pyridazine This compound was prepared using the procedure described in Example 1, Steps a), b) and c) using 4-methyltetrahydropyran-4-carboxylic acid (prepared using the conditions described in Example 36, Step a)) instead of cyclobutane carboxylic acid in Step a) and (1-methyl-1H-1,2,4-triazol-3-yl)methanol (prepared using the conditions described in EP-A-421210) instead of (2-methyl-2H-1,2,4-triazol-3-yl)methanol in Step c). Data for the title compound: m.p.=154° C.; $^1$H NMR (250 MHz, CDCl$_3$) δ 1.46 (3H, s), 1.93–1.99 (2H, m), 2.09–2.20 (2H, m), 3.77–3.80 (4H, m), 3.93 (3H, s), 5.44 (2H, s), 7.23–7.37 (2H, m), 7.49–7.58 (1H, m), 7.91 (1H, s), 7.97 (1H, m), 8.04 (1H, s); MS (ES$^+$) m/e 424 [MH]$^+$; Anal. Found: C, 59.26; H, 5.22; N, 22.79%. C$_{21}$H$_{22}$FN$_7$O$_2$ requires: C, 59.57; H, 5.24; N, 23.15%.

EXAMPLES 38 & 39

7-(4,4-Difluoro-1-methylcyclohexyl)-3-(2-fluorophenyl)-6-(2-methyl-2H-1,2,4-triazol-3-ylmethoxy)-1,2,4-triazolo[4,3-b]pyridazine and 7-(4-fluoro-1-methylcyclohex-3-enyl)-3-(2-fluorophenyl)-6-(2-methyl-2H-1,2,4-triazol-3-ylmethoxy)-1,2,4-triazolo[4,3-b]pyridazine a) 3,6-Dichloro-4-(1-methyl-4-oxocyclohexyl)pyridazine This compound was prepared using the procedure described in Example 1, Step a) using 1-methyl-4-oxocyclohexane carboxylic acid (*Aust. J. Chem.*, 1970, 23, 1005) instead of cyclobutane carboxylic acid. Data for the title compound: $^1$H NMR (360 MHz, CDCl$_3$) δ 1.63 (3H, s), 2.23–2.38 (4H, m), 2.46–2.55 (4H, m), 7.51 (1H, s); MS (ES$^+$) m/e 261 [MH]$^+$.

b) 3,6-Dichloro-4-(4,4-difluoro-1-methylcyclohexyl) pyridazine and 3,6-dichloro-4-(4-fluoro-1-methyl-cyclohex-3-enyl)pyridazine A solution of diethylaminosulfur trifluoride (1.2 ml, 9.13 mmol) in anhydrous dichloromethane (60 ml) under an atmosphere of nitrogen at −78° C. was added to a solution of 3,6-dichloro-4-(1-methyl-4-oxocyclohexyl)-pyridazine (1.08 g, 4.15 mmol) in anhydrous dichloromethane (140 ml) under nitrogen at −78° C. The reaction mixture was allowed to warm to room temperature slowly and was stirred for 5.5 days. The reaction mixture was poured onto saturated sodium bicarbonate and ice (250 ml), separated and the aqueous layer was extracted with dichloromethane (2×50 ml), organic layers were combined, washed with brine (250 ml), dried (MgSO$_4$), filtered and evaporated to yield the crude product which was purified by chromatography on silica gel eluting with 0%→20% ethyl acetate/hexane to give the title compounds (0.82 g, 70%) as a mixture in the ratio of 2.7:1. Data for the title compounds: $^1$H NMR (360 MHz, CDCl$_3$) δ 1.50 (2.2H, s), 1.54 (0.8H, s), 1.84–2.79 (7.3H, m), 5.20–5.29 (0.2H, m), 7.38 (0.2H, s), 7.46 (0.8H, s); MS (ES$^+$) m/e 282 [MH]+and m/e 262 [MH]$^+$.

c) 7-(4,4-Difluoro-1-methylcyclohexyl)-3-(2-fluorophenyl)-6-(2-methyl-2H-1,2,4-triazol-3-ylmethoxy)-1,2,4-triazolo [4,3-b]pyridazine and 7-(4-fluoro-1-methylcyclohex-3-enyl)-3-(2-fluorophenyl)-6-(2-methyl-2H-1,2,4-triazol-3-ylmethoxy)-1,2,4-triazolo[4,3-b]pyridazine The title compounds were prepared using the procedure described in Example 1, Steps b) and c) using a mixture of 3,6-dichloro-4-(4,4-difluoro-1-methylcyclohexyl) pyridazine and 3,6-dichloro-4-(4-fluoro-1-methyl-cyclohex-3-enyl)pyridazine instead of 3,6-dichloro-4-cyclobutylpyridazine in Step b). The compounds were separated by HPLC. Data for 7-(4,4-difluoro-1-methylcyclohexyl)-3-(2-fluorophenyl)-6-(2-methyl-2H-1,2,4-triazol-3-ylmethoxy)-1,2,4-triazolo[4,3-b]pyridazine: m.p.=135° C.; $^1$H NMR (250 MHz, CDCl$_3$) δ 1.42 (3H, s), 1.82–2.08 (6H, m), 2.16–2.34 (2H, m), 3.78 (3H, s), 5.53 (2H, s), 7.25–7.40 (2H, m), 7.58 (1H, m), 7.84 (1H, m), 7.89 (1H, s), 8.02 (1H, s); MS (ES$^+$) m/e 458 [MH]$^+$; Anal. Found: C, 55.36; H, 5.00; N, 18.96%. C$_{22}$H$_{22}$F$_3$N$_7$O.0.5 EtOAc.1.0H$_2$O requires: C, 55.48; H, 5.43; N, 18.87%. Data for 7-(4-fluoro-1-methylcyclohex-3-enyl)-3-(2-fluorophenyl)-6-(2-methyl-2H-1,2,4-triazol-3-ylmethoxy)-1,2,4-triazolo[4,3-b]pyridazine: m.p.=175° C.; $^1$H NMR (360 MHz, CDCl$_3$) δ 1.41 (3H, s), 1.76–1.98 (2H, m), 2.18–2.58 (4H, m), 3.78 (3H, s), 5.21–5.26 (1H, m), 5.53 (2H, s), 7.26–7.38 (2H, m), 7.54–7.59 (1H, m), 7.84 (1H, m), 7.89 (1H, s), 7.95 (1H, s); MS (ES$^+$) m/e 438 [MH]$^+$.

EXAMPLE 40

7-(4,4-Difluoro-1-methylcyclohexyl)-3-(2-fluorophenyl)-6-(1-methyl-1H-1,2,4-triazol-3-ylmethoxy)-1,2,4-triazolo [4,3-b]pyridazine This compound was prepared using the procedure described in Example 38, Steps a), b) and c) using (1-methyl-1H-1,2,4-triazol-3-yl)-methanol (prepared using the conditions described in EP-A-421210) instead of (2-methyl-2H-1,2,4-triazol-3-yl)methanol in Step c). Data for the title compound: m.p.=193° C.; $^1$H NMR (360 MHz, CDCl$_3$) δ 1.43 (3H, s), 1.88–2.12 (6H, m), 2.26–2.39 (2H, m), 3.92 (3H, s), 5.45 (2H, s), 7.24–7.35 (2H, m), 7.51–7.56 (1H, m), 7.94 (1H, m), 7.97 (1H, s), 8.04 (1H, s); MS (ES$^+$) m/e 458 [MH]$^+$; Anal. Found: C, 57.84; H, 4.75; N, 21.07%. C$_{22}$H$_{22}$F$_3$N$_7$O requires: C, 57.76; H, 4.85; N, 21.43%.

EXAMPLE 41

3-(2-Fluorophenyl)-6-(2-methyl-2H-1,2,4-triazol-3-ylmethoxy)-7-(3-oxocyclobutyl)-1,2,4-triazolo[4,3-b]pyridazine a) 7-(3-Benzyloxycyclobutyl)-6-chloro-3-(2-fluorophenyl)-1,2,4-triazolo[4,3-b]pyridazine This compound was prepared in a similar manner to that described for Example 1, Steps a) and b) using 3-benzyloxycyclobutane carboxylic acid (*Collect. Czech. Chem. Commun.*, 1982, 47, 2440) instead of cyclobutane carboxylic acid. Data for the title compound: $^1$H NMR (360 MHz, CDCl$_3$), cis and trans isomers present in 58:1 ratio, δ 2.06–2.51 (2H, m), 2.63–2.91 (2H, m), 3.13–3.25 (1H, m), 3.81–4.25 (1H, m), 4.50 (2H, s), 7.28–7.36 (7H, m), MS (ES$^+$) m/e 409 [MH]$^+$.

b) 7-(3-Benzyloxycyclobutyl)-3-(2-fluorophenyl)-1,2,4-triazolo[4,3-b]pyridazin-6-one 4N Sodium hydroxide (3 ml, 12 mmol) was added to a solution of 7-(3-benzyloxycyclobutyl)-6-chloro-3-(2-fluorophenyl)-1,2,4-triazolo[4,3-b]pyridazine (0.98 g, 2.4 mmol) in 1,4-dioxane (30 ml) and water (8 ml), heated to reflux for 18 hours. The solvent was evaporated and the residue dissolved in diethyl ether (50 ml) and water (50 ml) and separated. The aqueous layer was acidified to pH 2 with 2N hydrochloric acid and the resultant solid collected by filtration, washed with water (50 ml), followed by diethyl ether (50 ml) and dried under vacuum at 100° C. for 18 hours. Data for the title compound: $^1$H NMR (400 MHz, CDCl$_3$), cis and trans isomers present in 4:1 ratio, δ 1.95–2.03 (1.6H, m), 2.31–2.38 (0.4H, m), 2.50–2.56 (0.4H, m), 2.68–2.76 (1.6, m), 3.05–3.13 (1H, m), 3.65–3.73 (0.2H, m), 4.06–4.15 (0.8H, m), 4.46 (2H, s), 6.80–6.87 (2H, m), 7.22–7.37 (6H, m), 7.55–7.61 (1H, m), 7.63 (0.8H, m), 7.68 (0.2H, s); MS (ES$^+$) m/e 391 [MH]$^+$.

c) 3-(2-Fluorophenyl)-7-(3-hydroxycyclobutyl)-1,2,4-triazolo[4,3-b]pyridazin-6-one Formic acid (8 ml) was added to a solution of 7-(3-benzyloxy-cyclobutyl)-3-(2-fluorophenyl)-1,2,4-triazolo[4,3-b]pyridazin-6-one (0.64 g, 1.64 mmol) and ammonium for-mate (1.034 g, 16.4 mmol) in methanol (40 ml). The solution was flushed with nitrogen and 10% palladium on carbon (0.3 g) was added. The resulting solution was stirred under an atmosphere of nitrogen for 2 hours at 60° C. The reaction was cooled, filtered, and concentrated under vacuum. The residue was purified by chromatography on silica using 0–10% methanol/dichloromethane as eluent to give the required product as a white solid. Data for the title compound: $^1$H NMR (360 MHz, DMSO), cis and trans isomers present in 5.5:1 ratio, δ 1.89–1.98 (1.7H, m), 2.21–2.29 (0.3H, m), 2.40–2.48 (0.3H, m), 2.55–2.65 (1.7H, m), 2.88–3.00 (1H, m), 4.06–4.14 (0.85H, m), 4.20–4.30 (0.15H, m), 7.38–7.47 (2H, m), 7.60–7.65 (1H, m), 7.80–7.85 (1H, m), 7.97 (0.85H, s), 8.12 (0.15H, s); MS (ES$^+$) m/e 301 [H]$^+$.

d) 3-(2-Fluorophenyl)-7-(3-oxocyclobutyl)-1,2,4-triazolo[4,3-b]pyridazin-6-one

8N Chromic acid was added to a solution of 3-(2-fluorophenyl)-7-(3-hydroxycyclobutyl)-1,2,4-triazolo[4,3-b]pyridazin-6-one (0.36 g, 1.2 mmol) in acetone (50 ml) dropwise, until excess was present (red colour remained). The reaction was then stirred for 2 hours before isopropanol was added until the blue colour remained and no excess chromic acid was present. Water (50 ml) was added and the aqueous layer extracted with ethyl acetate (4×50 ml), organic layers were combined, washed with brine (50 ml), dried (MgSO$_4$), filtered and concentrated to give the desired product as a white solid. Data for the title compound: $^1$H NMR (360 MHz, DMSO) δ 3.41 (2H, s), 3.43 (2H, s), 3.73–3.78 (1H, m), 7.42–7.50 (2H, m), 7.64–7.72 (1H, m), 7.83–7.88 (1H, m), 8.38 (1H, s); MS (ES$^+$) m/e 299 [MH]$^+$.

e) 3-(2-Fluorophenyl)-6-(2-methyl-2H-1,2,4-triazol-3-ylmethoxy)-7-(3-oxocyclobutyl)-1,2,4-triazolo[4,3-b]pyridazine Sodium hydride (60% dispersion in oil, 62 mg, 1.54 mmol) was added to a stirred solution of 3-(2-fluorophenyl)-7-(3-oxocyclobutyl)-1,2,4-triazolo[4,3-b]pyridazin-6-one (0.23 g, 0.7 mmol) in anhydrous N,N-dimethylformamide (5 ml), and heated to 80° C. under an atmosphere of nitrogen for 0.5 hours. The solution was allowed to cool before addition of 5-chloromethyl-1-methyl-1H-1,2,4-triazole monohydrochloride (prepared using the conditions described in EP-A-170073) (0.14 g, 0.85 mmol). The reaction was then heated to 80° C., under an atmosphere of nitrogen, for 18 hours. The solution was allowed to cool, concentrated and the residue was purified by chromatography on silica using 0–5% methanol/dichloromethane as eluent to give the required product as a white solid. Data for the title compound: $^1$H NMR (360 MHz, CDCl$_3$) δ 3.29–3.38 (2H, m), 3.45–3.56 (2H, m), 3.73–3.82 (4H, m), 5.52 (2H, s), 7.26—7.31 (1H, m), 7.35–7.39 (1H, m), 7.56–7.60 (1H, m), 7.81–7.85 (1H, m), 7.88 (1H, s), 7.98 (1H, s); MS (ES$^+$) m/e 394 [MH]$^+$.

EXAMPLE 42

7-(3,3-Difluorocyclobutyl)-3-(2-fluorophenyl)-6-(2-methyl-2H-1,2,4-triazol-3-ylmethoxy)-1,2,4-triazolo[4,3-b]pyridazine A solution of diethylaminosulfur trifluoride (0.074 ml, 0.56 mmol) in anhydrous dichloromethane (6 ml) under nitrogen at −78° C. was added to a solution of 3-(2-fluorophenyl)-6-(2-methyl-2H-1,2,4-triazol-3-ylmethoxy)-7-(3-oxocyclobutyl)-1,2,4-triazolo[4,3-b]pyridazine (0.1 g, 0.254 mmol) in anhydrous dichloromethane (14 ml) under nitrogen at −78° C. The reaction mixture was allowed to warm to room temperature slowly and stirred for 4 days. The reaction had not gone to completion; thus a further 0.037 ml of diethylaminosulfur trifluoride (0.28 mmol) was added at −78° C. After a further 2 days at room temperature there was still starting material remaining; thus a further 0.074 ml of diethylaminosulfur trifluoride (0.56 mmol) was added at −78° C. Thus a total of 5.5 eq of diethylaminosulfur trifluoride was added over a 10-day period. The solution was added to saturated sodium bicarbonate and ice (25 ml), separated and the aqueous layer was extracted with dichloromethane (2×25 ml), organic layers were combined, washed with brine (25 ml), dried (MgSO$_4$), filtered and evaporated. The residue was purified by chromatography on silica gel eluting with 0%→5% methanol/dichloromethane and recrystallised from ethyl acetate/isohexane to give the title compound as a pale orange solid. Data for the title compound: m.p.=178° C.; $^1$H NMR (400 MHz, CDCl$_3$) δ 2.70–2.78 (2H, m), 3.00–3.07 (2H, m), 3.47–3.50 (1H, m), 3.80 (3H, s), 5.50 (2H, s), 7.25–7.30 (1H, m), 7.34–7.38 (1H, m), 7.56–7.59 (1H, m), 7.80–7.85 (1H, m), 7.89 (1H, s), 7.90 (1H, s); MS (ES$^+$) m/e 416 [MH]$^+$; Anal. Found: C, 55.55; H, 3.99; N, 23.37%. C$_{19}$H$_{16}$F$_3$N$_7$O requires: C, 54.94; H, 3.88; N, 23.60%.

EXAMPLE 43

3-(2-Fluorophenyl)-6-(2-methyl-2H-1,2,4-triazol-3-ylmethoxy)-7-(tetrahydrofur-2-yl)-1,2,4-triazolo[4,3-b]pyridazine This compound was prepared using the procedures described in Example 1 Steps a), b) and c) using tetrahydro-2-furoic acid instead of cyclobutane carboxylic acid in Step a). Data for the title compound: m.p.136–139° C.; $^1$H NMR (360 MHz, CDCl$_3$) δ 1.77 (1H, m), 1.98 (2H, m), 2.42 (1H, m), 3.82 (3H, s), 3.98 (1H, q, J=7.1 & 15.4 Hz), 4.15 (1H, m), 5.01 (1H, t, J=6.3 Hz), 5.51 (2H, q, J=13.1 & 22.0 Hz), 7.25–7.38 (2H, m), 7.55 (1H, m), 7.85 (1H, m), 7.89 (1H, s), 8.18 (1H, s); MS (ES$^+$) m/e 396 [MH]$^+$.

EXAMPLE 44

7-(3-Fluorophenyl)-3-(2-fluorophenyl)-6-(2-methyl-2H-1,2,4-triazol-3-ylmethoxy)-1,2,4-triazolo[4,3-b]pyridazine A stirred mixture of 7-bromo-3-(2-fluorophenyl)-6-(2-methyl-2H-1,2,4-triazol-3-ylmethoxy)-1,2,4-triazolo[4,3-b]

pyridazine (50.2 mg, 0.124 mmol), 3-fluorobenzeneboronic acid (24.7 mg, 0.177 mmol), potassium phosphate (74.1 mg, 0.339 mmol), and tetrakis(triphenylphosphine)-palladium (0) (11.5 mg, 0.00995 mmol) in anhydrous DMF (3 ml) was degassed by evaporating and refilling the flask with nitrogen four times, then heated at 100° C. under nitrogen for 14.5 h. The mixture was partitioned between ethyl acetate (20 ml) and brine (15 ml). The aqueous layer was further extracted with ethyl acetate (2×20 ml) and the combined organic extracts were evaporated in vacuo. The residue was purified by flash chromatography (silica gel, 2% MeOH/$CH_2Cl_2$) to afford 18.1 mg (35%) of the title compound as a white solid: m.p. 204–206° C. ($CH_2Cl_2$-EtOAc-hexane); $^1$H NMR (360 MHz, $CDCl_3$) δ 3.70 (3H, s), 5.54 (2H, s), 7.18 (1H, m), 7.28–7.40 (4H, m), 7.46 (1H, m), 7.58 (1H, m), 7.86 (1H, s), 7.88 (1H, td, J=7.5 and 1.8 Hz), 8.08 (1H, s); MS ($ES^+$) m/e 420 $[MH]^+$.

What is claimed is:

1. A compound of the formula I:

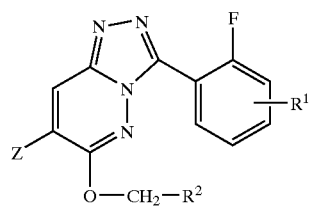

(I)

wherein:

Z represents cyclobutyl, 1-methylcyclobutyl or 1-fluorocyclobutyl;

$R^1$ represents hydrogen or fluoro, with the proviso that $R^1$ is located other than at the 6-position of the phenyl ring;

$R^2$ represents methyl-pyrazolyl, methyl-imidazolyl, benzimidazolyl or methyl-triazolyl; or a pharmaceutically acceptable salt thereof.

2. The compound of claim 1 wherein Z represents cyclobutyl.

3. The compound of claim wherein $R^2$ represents a ring of structure (b), (c), (d), (e), (f) or (g):

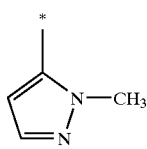

(b)

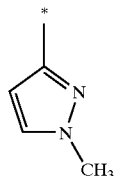

(c)

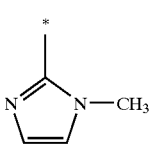

(d)

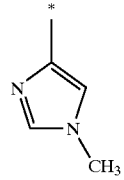

(e)

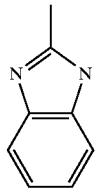

(f)

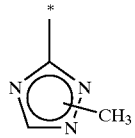

(g)

where the asterisk * denotes the point of attachment of the ring to the remainder of the molecule.

4. The compound of claim 3 wherein $R^2$ represents a ring of structure (g):

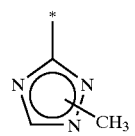

(g)

where the asterisk * denotes the point of attachment of the ring to the remainder of the molecule.

5. The compound of claim 1 of the formula IIA:

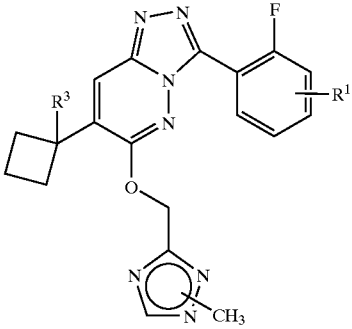

(IIA)

wherein $R^1$ represents hydrogen or fluoro, with the proviso that $R^1$ is located other than at the 6-position of the phenyl ring;

$R^3$ represents hydrogen or fluoro; or a pharmaceutically acceptable salt thereof.

6. The compound of claim 1 of the formula IIB:

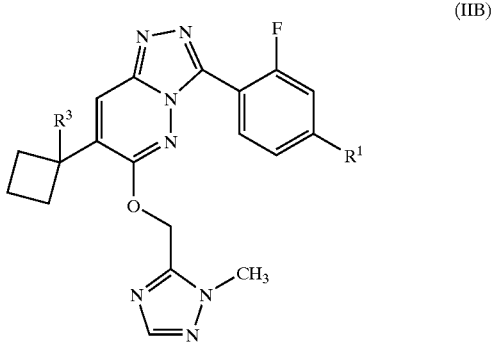

(IIB)

wherein
R¹ represents hydrogen or fluoro; and
R³ represents hydrogen or fluoro.

7. The compound of claim 1 wherein R³ represents hydrogen.

8. A compound which is selected from the group consisting of:
  7-cyclobutyl-3-(2-fluorophenyl)-6-(2-methyl-2H-1,2,4-triazol-3-ylmethoxy)-1,2,4-triazolo[4,3-b]pyridazine;
  7-cyclobutyl-3-(1-fluorophenyl)-6-(1-methyl-1H-1,2,4-triazol-3-ylmethoxy)-1,2,4-triazolo[4,3-b]pyridazine;
  7-cyclobutyl-3-(2,4-difluorophenyl)-6-(2-methyl-2H-1,2,4-triazol-3-ylmethoxy)-1,2,4-triazolo[4,3-b]pyridazine;
  3-(2,4-difluorophenyl)-7-(1-methylcyclobutyl)-6-(2-methyl-2H-1,2,4-triazol-3-ylmethoxy)-1,2,4-triazolo[4,3-b]pyridazine;
  7-cyclobutyl-3-(2,3-difluorophenyl)-6-(2-methyl-2H-1,2,4-triazol-3-ylmethoxy)-1,2,4-triazolo[4,3-b]pyridazine;
  7-cyclobutyl-3-(2,5-difluorophenyl)-6-(2-methyl-2H-1,2,4-triazol-3-ylmethoxy)-1,2,4-triazolo [4,3-b]pyridazine;
  3-(2,4-difluorophenyl)-7-(1-methylcyclohexyl)-6-(2-methyl-2H-1,2,4-triazol-3-ylmethoxy)-1,2,4-triazolo[4,3-b]pyridazine;
  3-(2,4-difluorophenyl)-7-(1-methylcyclohexyl)-6-(1-methyl-1H-1,2,4-triazol-3-ylmethoxy)-1,2,4-triazolo[4,3-b]pyridazine;
  7-cyclobutyl-3-(2-fluorophenyl)-6-(1-methyl-1H-pyrazol-3-ylmethoxy)-1,2,4-triazolo[4,3-b]pyridazine;
  7-cyclobutyl-3-(2-fluorophenyl)-6-(5-methylisoxazol-3-ylmethoxy)-1,2,4-triazolo[4,3-b]pyridazine;
  7-cyclobutyl-3-(2-fluorophenyl)-6-(1-methyl-1H-imidazol-2-ylmethoxy)-1,2,4-triazolo[4,3-b]pyridazine;
  7-cyclobutyl-3-(2-fluorophenyl)-6-(4-methyl-4H-1,2,4-triazol-3-ylmethoxy)-1,2,4-triazolo[4,3-b]pyridazine;
  3-(2-fluorophenyl)-6-(2-methyl-2H-1,2,4-triazol-3-ylmethoxy)-7-(thien-2-yl)-1,2,4-triazolo[4,3-b]pyridazine;
  3-(2,4-difluorophenyl)-6-(2-methyl-2H-1,2,4-triazol-3-ylmethoxy)-7-(thien-2-yl)-1,2,4-triazolo[4,3-b]pyridazine;
  6-(1H-benzimidazol-2-ylmethoxy)-7-cyclobutyl-3-(2,4-difluorophenyl)-1,2,4-triazolo[4,3-b]pyridazine;
  7-cyclobutyl-3-(2-fluorophenyl)-6-(1-methyl-1H-imidazol-4-ylmethoxy)-1,2,4-triazolo[4,3-b]pyridazine;
  7-(1-fluorocyclobutyl)-3-(2-fluorophenyl)-6-(2-methyl-2H-1,2,4-triazol-3-ylmethoxy)-1,2,4-triazolo[4,3-b]pyridazine;
  7-cyclobutyl-3-(2-fluorophenyl)-6-(2-methyl-2H-pyrazol-3-ylmethoxy)-1,2,4-triazolo[4,3-b]pyridazine;
and pharmaceutically acceptable salts thereof.

9. A pharmaceutical composition comprising a compound of claim 1 or a pharmaceutically acceptable salt thereof and a pharmaceutically acceptable carrier.

10. A method for the treatment of anxiety which comprises administeping to a patient in need thereof an effective amount of a compound of claim 1 or a pharmaceutically acceptable salt thereof.

11. A method for the prevention of anxiety which comprises administering to a patient in need thereof an effective amount of a compound of claim 1 or a pharmaceutically acceptable salt thereof.

12. A method for the treatment of convulsions which comprises administering to a patient in need thereof an effective amount of a compound of claim 1 or a pharmaceutically acceptable salt thereof.

13. A method for the prevention of convulsions which comprises administering to a patient in need thereof an effective amount of a compound of claim 1 or a pharmaceutically acceptable salt thereof.

14. A method for the treatment of migraine comprising administering to a patient in need thereof an effective amount of a compound according to claim 1 or a pharmaceutically acceptable salt thereof.

15. A method for the prevention of migraine comprising administering to a patient in need thereof an effective amount of a compound according to claim 1 or a pharmaceutically acceptable salt thereof.

* * * * *